(12) United States Patent
Min et al.

(10) Patent No.: US 10,781,001 B2
(45) Date of Patent: Sep. 22, 2020

(54) FILL AND FINISH SYSTEMS AND METHODS

(71) Applicant: Fenwal, Inc., Lake Zurich, IL (US)

(72) Inventors: Kyungyoon Min, Kildeer, IL (US); Alexandra Salomon, Evanston, IL (US); Julie Griep, St. Paul, MN (US); Christopher J. Wegener, Liberty, IL (US)

(73) Assignee: Fenwal, Inc., Lake Zurich, IL (US)

( * ) Notice: Subject to any disclaimer, the term of this patent is extended or adjusted under 35 U.S.C. 154(b) by 189 days.

(21) Appl. No.: 15/702,894

(22) Filed: Sep. 13, 2017

(65) Prior Publication Data

US 2018/0155070 A1    Jun. 7, 2018

Related U.S. Application Data

(60) Provisional application No. 62/429,050, filed on Dec. 1, 2016.

(51) Int. Cl.
| | |
|---|---|
| *B65B 3/26* | (2006.01) |
| *B65B 3/00* | (2006.01) |
| *A61M 1/02* | (2006.01) |
| *B67C 3/12* | (2006.01) |
| *A61J 1/20* | (2006.01) |
| *A61M 1/34* | (2006.01) |
| *A61M 1/36* | (2006.01) |

(Continued)

(52) U.S. Cl.
CPC .............. *B65B 3/26* (2013.01); *A61J 1/2003* (2015.05); *A61M 1/0209* (2013.01); *A61M 1/34* (2013.01); *A61M 1/3693* (2013.01); *B65B 3/003* (2013.01); *B65B 3/12* (2013.01); *B67C 3/12* (2013.01); *A61M 1/265* (2014.02); *A61M 2205/3331* (2013.01); *A61M 2205/50* (2013.01)

(58) Field of Classification Search
CPC . B65B 3/003; B65B 3/14; B65B 3/12; A61M 5/1456; A61M 5/14526; A61M 5/1782; B05C 17/015
See application file for complete search history.

(56) References Cited

U.S. PATENT DOCUMENTS

| | | |
|---|---|---|
| 5,053,121 A | 10/1991 | Schoendorfer et al. |
| 5,194,145 A | 3/1993 | Schoendorfer |
| (Continued) | | |

FOREIGN PATENT DOCUMENTS

| | | |
|---|---|---|
| EP | 1254675 | 11/2002 |
| WO | WO2012/125457 | 9/2012 |
| (Continued) | | |

OTHER PUBLICATIONS

U.S. Appl. No. 15/703,067, filed Sep. 13, 2017.
European Patent Office, Partial European Search Report, counterpart EP Appl. No. 17190842, dated Apr. 3, 2018.

*Primary Examiner* — Timothy P. Kelley
(74) *Attorney, Agent, or Firm* — Cook Alex Ltd.

(57) ABSTRACT

A variety of fill options is provided for a cell processing system. Certain options relate to a filling system associated with the cell processing system, the filling system comprising one or more filling stations, each with at least one container that may receive product from a container associated with a cell processing system. Other options relate to a syringe assembly that receives a product from a container associated with a cell processing system.

11 Claims, 17 Drawing Sheets

(51) Int. Cl.
*B65B 3/12* (2006.01)
*A61M 1/26* (2006.01)

(56) References Cited

U.S. PATENT DOCUMENTS

| | | |
|---|---|---|
| 5,697,407 A | 12/1997 | Lasonde |
| 5,789,147 A | 8/1998 | Rubinstein et al. |
| 5,840,502 A | 11/1998 | Van Vlasselaer |
| 6,464,624 B2 | 10/2002 | Pages |
| 6,709,378 B2 | 3/2004 | Nishimura et al. |
| 6,716,151 B2 | 4/2004 | Panzani et al. |
| 6,733,433 B1 | 5/2004 | Fell |
| 7,011,852 B2 | 3/2006 | Sukavaneshvar et al. |
| 7,179,391 B2 | 2/2007 | Leach et al. |
| 7,291,450 B2 | 11/2007 | Sowemimo-Coker et al. |
| 7,364,657 B2 | 4/2008 | Mandrusov et al. |
| 7,374,678 B2 | 5/2008 | Leach et al. |
| 8,101,077 B2 | 1/2012 | Sukavaneshvar et al. |
| 8,439,889 B2 | 5/2013 | Sano |
| 8,808,551 B2 | 8/2014 | Leach et al. |
| 8,961,787 B2 | 2/2015 | Wood et al. |
| 8,986,185 B2 | 3/2015 | Del Vecchio |
| 9,033,948 B2 | 5/2015 | Payrat et al. |
| 9,352,021 B2 | 5/2016 | Hanna et al. |
| 9,452,254 B2 | 9/2016 | Kimura et al. |
| 9,459,186 B2 | 10/2016 | Mastromatteo et al. |
| 9,603,986 B2 | 3/2017 | Kusters et al. |
| 9,717,842 B2 | 8/2017 | Min et al. |
| 9,724,268 B2 | 8/2017 | Bertoni |
| 9,907,899 B2 | 3/2018 | Kim |
| 10,625,003 B2 | 4/2020 | Bertoni |
| 2003/0230521 A1 | 12/2003 | Schick |
| 2006/0224144 A1* | 10/2006 | Lee ............. A61M 1/0009 604/542 |
| 2008/0171951 A1 | 7/2008 | Fell |
| 2011/0124106 A1 | 5/2011 | Froman et al. |
| 2013/0092630 A1 | 4/2013 | Wegener |
| 2013/0240082 A1 | 9/2013 | Mueller |
| 2015/0080204 A1 | 3/2015 | Kassis |
| 2015/0190578 A1* | 7/2015 | Okihara ............. A61M 5/28 53/432 |
| 2016/0151570 A1* | 6/2016 | Rhinehart ......... A61M 5/1782 604/149 |
| 2016/0252434 A1 | 9/2016 | Smith et al. |
| 2017/0204371 A1 | 7/2017 | Wegener |
| 2017/0262601 A1 | 9/2017 | Binninger et al. |
| 2017/0340783 A1 | 11/2017 | Wegener et al. |
| 2018/0015418 A1 | 1/2018 | Binninger et al. |
| 2018/0072977 A1 | 3/2018 | Binninger |
| 2020/0046899 A1* | 2/2020 | Cane' ............. A61M 5/14526 |

FOREIGN PATENT DOCUMENTS

| | | |
|---|---|---|
| WO | WO2012/125470 | 9/2012 |
| WO | WO2014/108852 | 7/2014 |
| WO | WO2016/098007 | 6/2016 |

\* cited by examiner

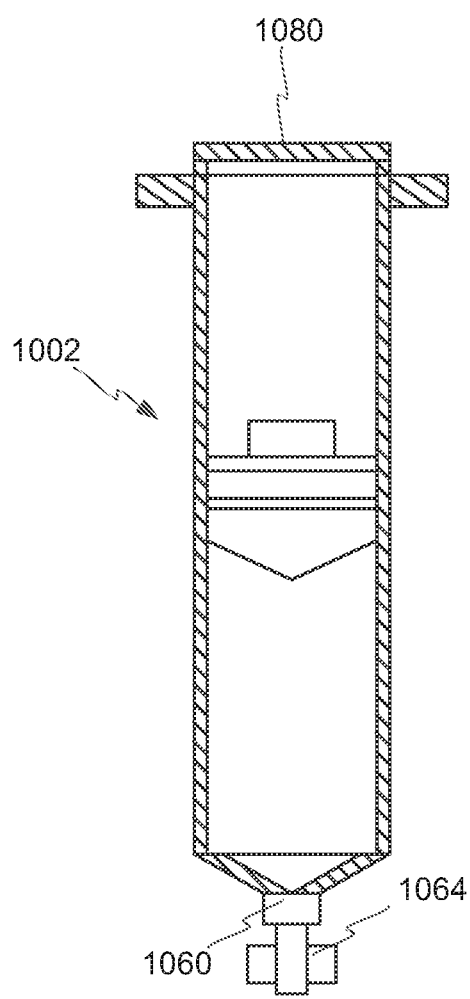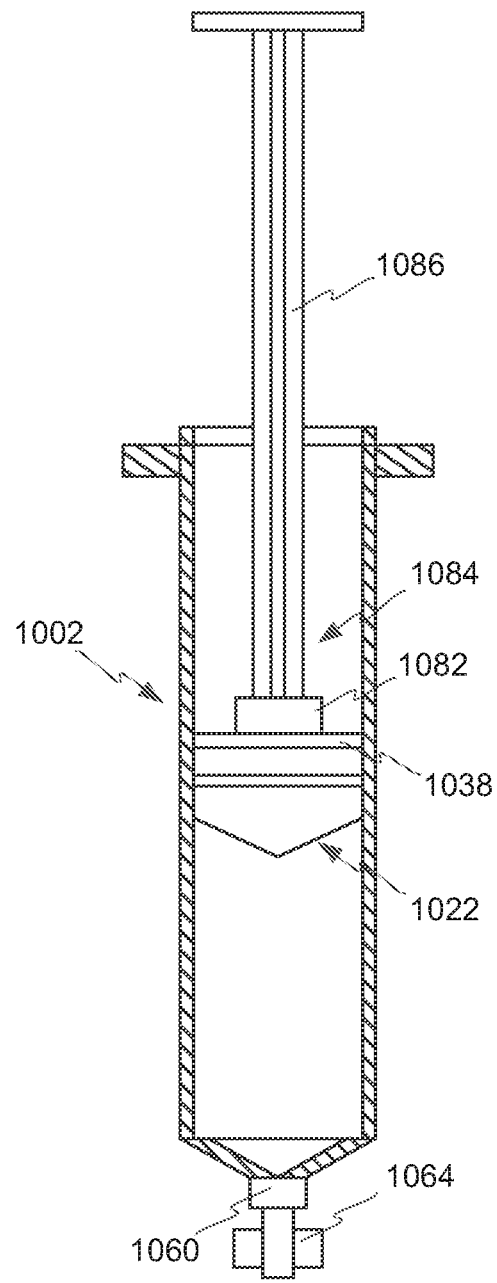
*FIG. 27*   *FIG. 28*

FILL AND FINISH SYSTEMS AND METHODS

CROSS-REFERENCE TO RELATED APPLICATIONS

This application claims the benefit of U.S. Provisional Application No. 62/429,050, filed Dec. 1, 2016, which is hereby incorporated herein by reference.

TECHNICAL FIELD

The present disclosure is generally directed to systems and methods for filling a product, such as a cell product, into one or more containers. More particularly, the present disclosure is directed to the processing of biological fluid using a disposable fluid circuit and a reusable processing machine to generate a product, and systems and methods for filling the product into one or more containers, including end-user containers.

BACKGROUND

The processing of biological fluid such as blood or blood components typically involves using a reusable processing machine ("hardware") and a disposable fluid circuit adapted for mounting or other association with the reusable apparatus. The fluid circuit typically includes (plastic) bags and associated tubing that defines a flow path through the circuit. The disposable fluid circuit may also include one or more separation devices where the biological fluid/cells can be separated into two or more components, washed or otherwise processed. Separation devices may separate the biological fluid based on centrifugal separation and/or, as described below, membrane separation.

Conventionally, the product is directed into a product container, such as a flexible walled bag. At the time of use, the product may be removed from the bag via a port or port assembly. In particular, one or more syringes may be connected to the port, and then the product from the bag is drawn into the syringe. Consequently, cells may be left in the product bag and not transferred to the syringes. Further, the method provides the potential for contamination of the product in the syringe if proper sterilization protocols are not used.

SUMMARY

In one aspect, a filling system includes a transfer set connectable to a source container, a plurality of filling stations each comprising at least one container connected to the transfer set and in selective fluid communication with the source container via the transfer set, a pump configured to transfer a product from the source container to the at least one container via the transfer set and a controller. The controller is coupled to the at least one filling station and the pump, and is configured to operate each of the filling stations and the pump in concert to move fluid from the source container to the at least one container associated with at least one of the plurality of filling stations.

According to another aspect, a filling system for filling a pre-filled syringe from a source container includes a transfer set connectable to a source container, a syringe having a first end to a first side of a plunger head assembly detachably connected to the transfer set, and a second end to a second side of the plunger head assembly, a pump detachably connected to the second side of the plunger head assembly, and a controller coupled to the pump. The controller is configured to operate the pump to move the plunger head assembly between the first end and the second end to fill the syringe.

BRIEF DESCRIPTION OF THE FIGURES

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

FIG. 27 is a cross-sectional view of a pre-filled syringe produced using the embodiment of FIG. 20; and FIG. 28 is a cross-sectional view of the pre-filled syringe of FIG. 27 configured for administration to a patient.

DETAILED DESCRIPTION

Figure 1:
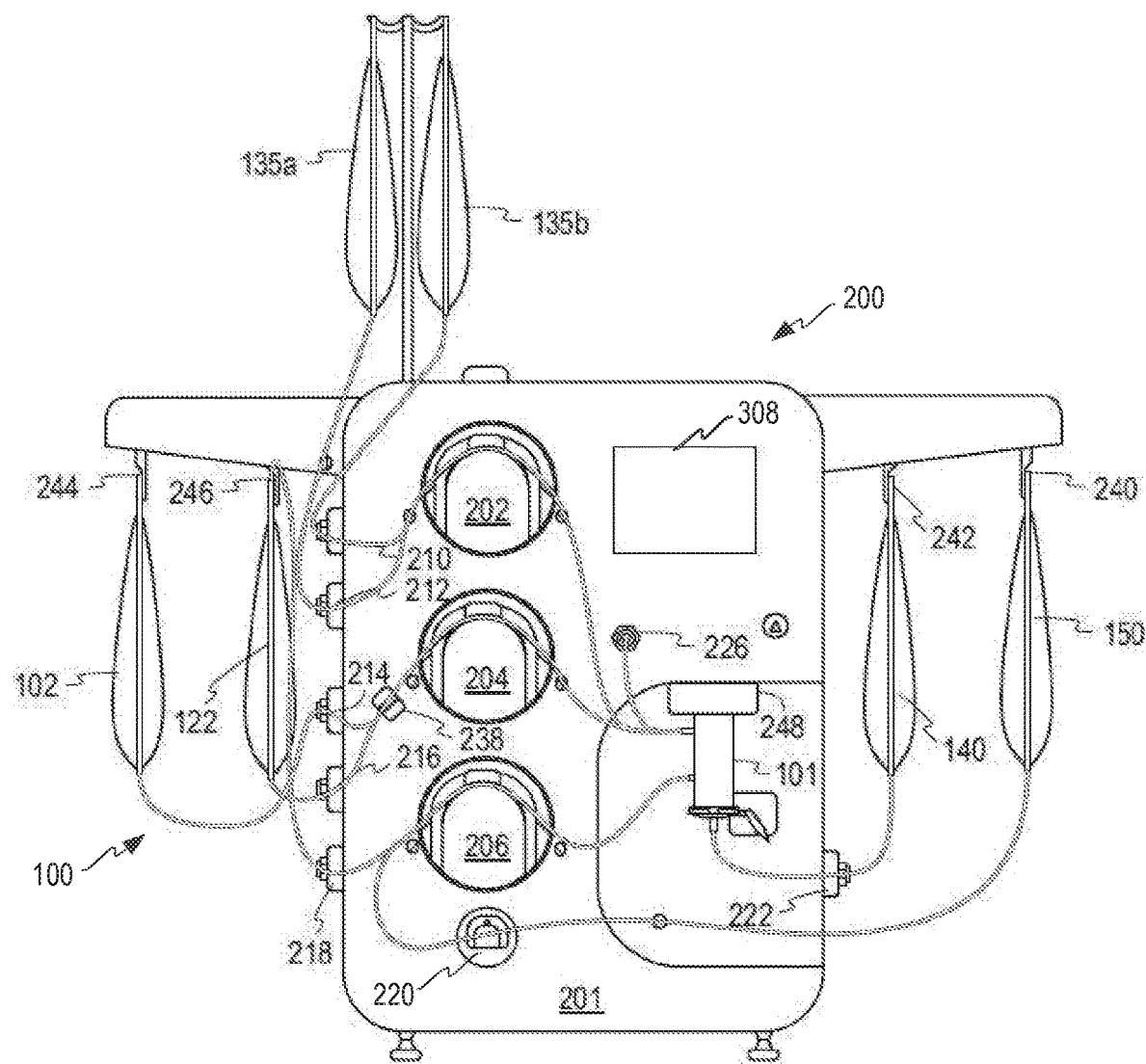
FIG. 1 is a frontal view of a reusable cell processing apparatus with a disposable fluid circuit loaded thereon.
Figure 2:
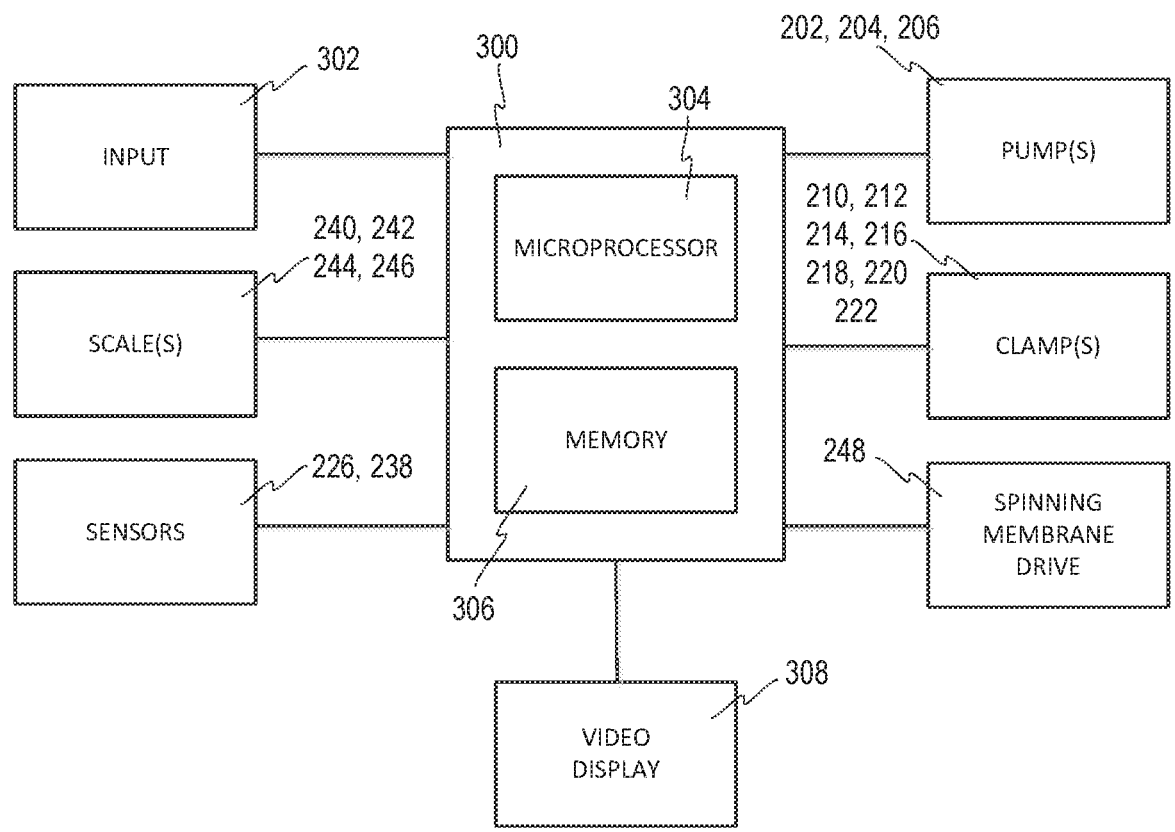
FIG. 2 is a schematic view of the control circuitry of the apparatus of FIG. 1.

As illustrated in FIGS. 1 and 2, a cell processing system includes a processor 100, 200 to receive a biological fluid to be processed, and a control unit (or controller) 300 coupled to the processor 100, 200, the controller 300 configured to operate the processor 100, 200 according to a procedure or process to produce or generate a product that is disposed in a product container. According to the embodiments described herein, the cell processing system may be used in conjunction with a number of fill options, as illustrated in FIGS. 7-28. According to those fill options, a filling system may be used to distribute product from the product container such as may be produced or generated by the processor 100, 200 into a plurality of other containers for storage, shipment, or both after processing of the biological fluid. The filling systems described herein are not restricted, however, to being used with product as may be produced as a consequence of the operation of a processor 100, 200 such as is illustrated in FIGS. 1-6, but may be used with product produced using other systems and methods.

As explained in detail below, the processor 100, 200 may include a disposable processing fluid circuit 100 (see also FIG. 3) and reusable hardware 200 (see also FIG. 4). According to the illustrated embodiments in FIGS. 1 and 3, the disposable fluid circuit 100 may include a spinning membrane 101, at least one container 102, 122, 135*a*, 135*b*, 140, 150 and tubing 106, 120, 128, 132*a*, 132*b*, 162, 166, 168 connecting the spinning membrane 101 and the one or more containers 102, 122, 135*a*, 135*b*, 140, 150. As is also illustrated, the reusable hardware 200 may include at least one drive 248 to spin the spinning membrane 101, at least one scale 240, 242, 244, 246 to weigh the at least container 102, 122, 140, 150 and contents thereof, and at least one pump 202, 204, 206 to receive the tubing 162, 166, 168 and pump fluid through the tubing 162, 166, 168 by peristaltic action, for example, although other types of pumps and pumping action may be used. The controller 300 may, according to the embodiments, include a programmable microprocessor 304, which microprocessor 304 may be coupled to the at least one input 302 and may be programmed to operate the processor according to a process.

Thus, the cell processing systems disclosed herein typically include a reusable separation apparatus and one or more disposable processing circuits adapted for association with the reusable apparatus, which apparatus and circuit(s) define the processor. The reusable separation apparatus may be any apparatus that can provide for the automated processing of biological fluid. "Biological fluid" includes without limitation blood and blood components, and "cell" or "biological cell" includes without limitation blood cells, such as red cells, white cells and platelets. By "automated," it is meant that the apparatus can be programmed to carry out the processing steps of a biological fluid processing method without substantial operator involvement. Of course, even in the automated system of the present disclosure, it will be understood that operator activity may be involved, including the loading of the disposable fluid circuits and entering processing parameters. Additional manual steps may be required as well. However, the reusable apparatus can process biological fluid through the disposable circuit(s) described below without substantial operator intervention.

Figure 6:
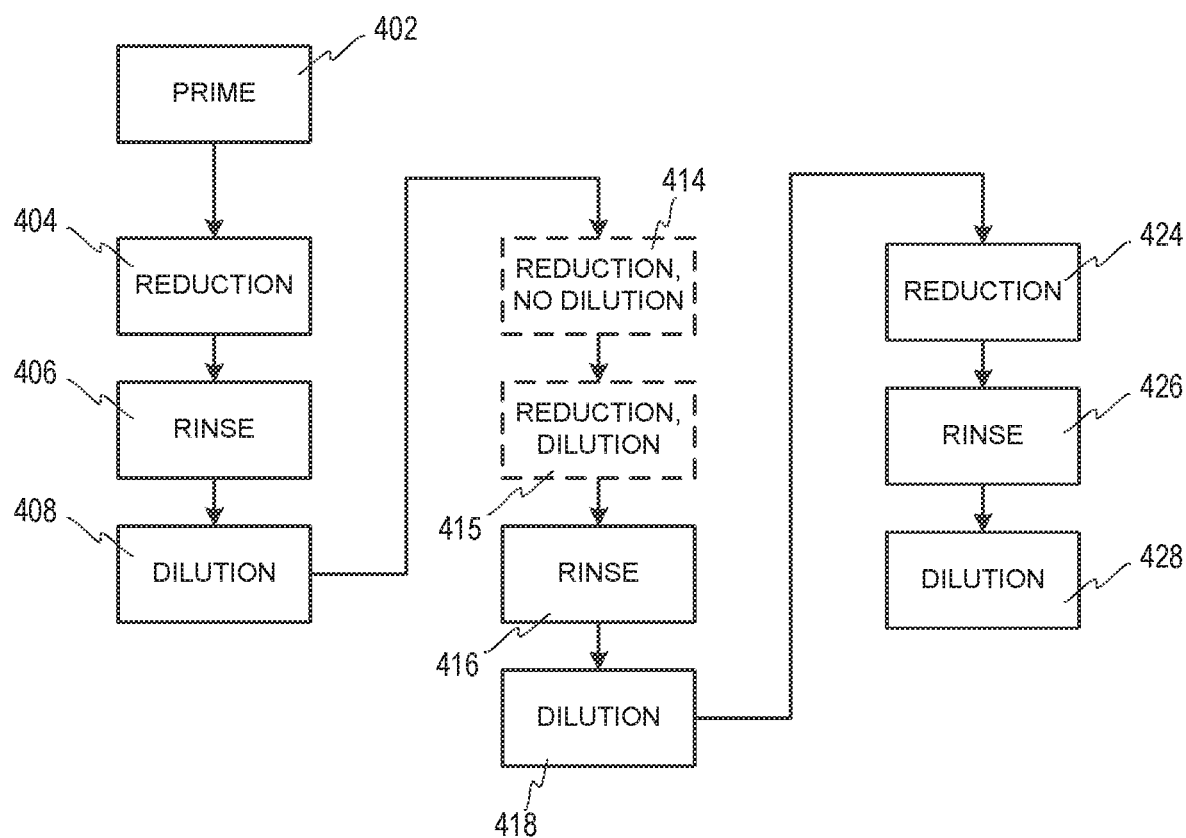
FIG. 6 is a flowchart of one embodiment of a method of operating a reusable cell processing apparatus with a disposable fluid circuit loaded thereon, such as is illustrated in FIG. 1, to process a biological fluid.
Figure 7:
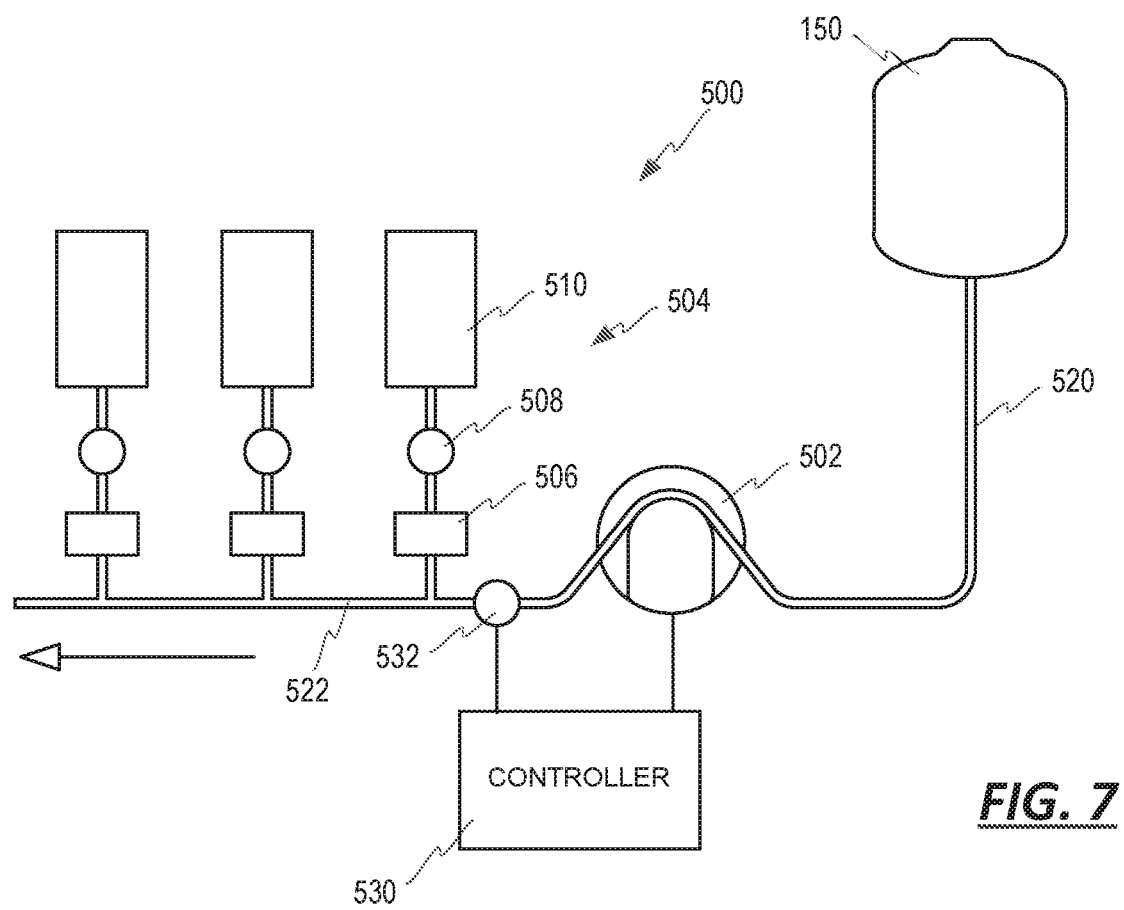
FIG. 7 is a schematic diagram of an embodiment of a filling system for use with a product container, such as may be produced in accordance with the embodiment of FIGS. 1-6.

The illustrated processing apparatus is typically capable of effecting the separation of a biological fluid that includes biological cells into two or more components or fractions. Thus, the reusable apparatus may generate conditions that allow for the separation of a biological fluid into selected components or fractions. One preferred machine for separating biological fluid into its constituent components or fractions uses a spinning porous membrane. An example of such machine is the Autopheresis C® sold by Fenwal, Inc. of Lake Zurich, Ill., which is an affiliate of Fresenius Kabi AG of Bad Homburg, Germany. A detailed description of a spinning membrane may be found in U.S. Pat. No. 5,194,145 to Schoendorfer, which is incorporated by reference herein in its entirety, and in International (PCT) Application No. PCT/US2012/028492, filed Mar. 9, 2012, the contents of which are also incorporated herein in their entirety. In addition, systems and methods that utilize a spinning porous membrane are also disclosed in U.S. Provisional Patent Application No. 61/537,856, filed on Sep. 22, 2011 and International (PCT) Application No. PCT/US2012/028522, filed Mar. 9, 2012, the contents of each are incorporated herein by reference. The references identified above describe a membrane-covered spinner having an interior collection system disposed within a stationary shell. While a detailed discussion of the separation device is beyond the scope of this application, the spinning membrane separation device is shown in FIGS. 6, 7(*a*)-7(*b*) of the reference cited and is discussed below in general terms. In another embodiment, the reusable apparatus may generate a centrifugal field to effect separation.

Figure 3:
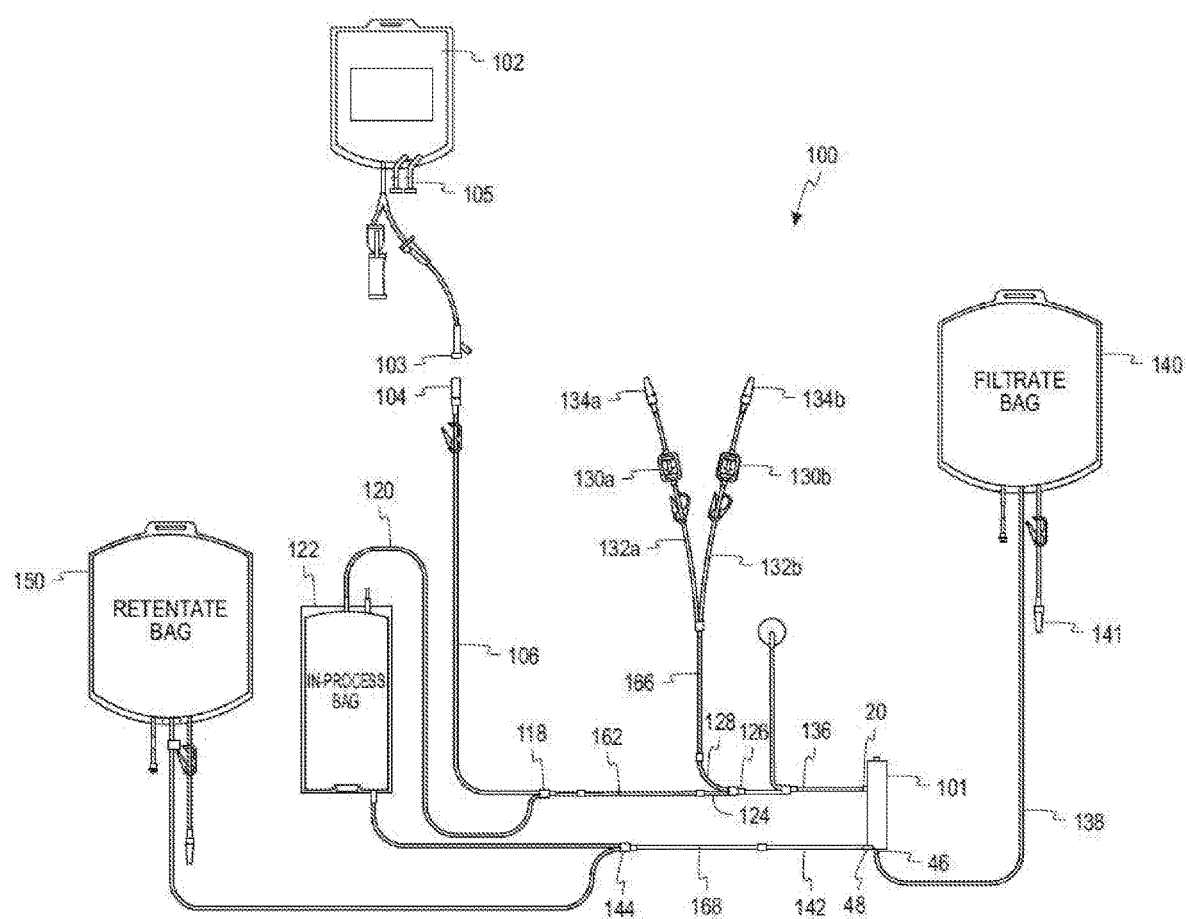
FIG. 3 is a schematic view of one embodiment of a disposable fluid circuit useful in the systems and methods described herein.

Turning now to FIG. 3, the systems described herein include at least one disposable fluid circuit 100 for use in the processing of biological fluid. While the circuits described herein may be used as stand-alone circuits, more preferably, at least two or more disposable fluid circuits are used in combination and in series for the separation, washing, volume reduction and/or other processing of a biological fluid. Circuit 100 may include an integrated separation device, such as, but not limited to, the spinning membrane 101 described above. Circuit 100 may also include waste container 140, product container 150, and in-process container 122. Disposable fluid circuits of the type described below may further include sampling assemblies (not shown) for collecting samples of source biological fluid, "final" product, or other intermediate products obtained during the biological fluid processing.

As will be seen in the Figures and described in detail below, the disposable fluid processing circuits include tubing that defines flow paths throughout the circuits, as well as access sites for sterile or other connection to containers of processing solutions, such as wash solutions, treating agents, or sources of biological fluid. As shown in FIG. 3, the tubing of circuit 100 includes spaced tubing segments identified by reference numerals 162, 166, 168. The tubing segments are provided for mating engagement with the peristaltic pumps 202, 204, 206 of the reusable hardware apparatus 200 discussed below. The containers and the plastic tubing are made of conventional medical grade plastic that can be sterilized by sterilization techniques commonly used in the medical field such as, but not limited to, radiation or autoclaving. Plastic materials useful in the manufacture of containers and of the tubing in the circuits disclosed herein include plasticized poly(vinyl chloride). Other useful materials include acrylics. In addition, certain polyolefins may also be used.

As will be apparent from the disclosure herein, source containers may be attached in sterile fashion to the circuit 100. Source containers 102 for connection to one disposable circuit may be the product containers 150 of another circuit used in an earlier step of the overall method of processing. Alternatively, the contents of a product container 150 may be further processed or separated and then transferred in sterile fashion to the source container 102 of a later-in-series fluid circuit.

The biological cell suspension to be washed or otherwise treated is typically provided in a source container 102, shown in FIG. 3 as (initially) not connected to the disposable set. As noted above, source container 102 may be attached (in sterile fashion) at the time of use. Source container 102 has one or more access sites 103, 105, one of which may be adapted for (sterile) connection to fluid circuit 100 at docking site 104. Preferably, source containers may be attached in a sterile manner by employing sterile docking devices, such as the BioWelder, available from Sartorius AG, or the SCD IIB Tubing Welder, available from Terumo Medical Corporation. A second access port 105 may also be provided for extracting fluid from the source container 102.

As further shown in FIG. 3, tubing segment 106 extends from docking site 104 and is connected to further downstream branched-connector 118. Branched-connector 118 communicates with tubing 106 and tubing 120, which provides a fluid flow path from "in-process" container 122, described in detail below. Tubing segment 124 extends from branched-connector 118 and is joined to a port of further downstream branched-connector 126. A separate flow path defined by tubing 128 is also connected to a port of branched-connector 126.

In accordance with the fluid circuit of FIG. 3, one or more containers of wash or other processing/treating solution may be attached (or pre-attached) to set 100. As shown in FIG. 3, tubings 132a, 132b (defining a flow path) preferably include and terminate in an access site such as spike connectors 134a, 134b. Access sites 134a, 134b are provided to establish flow communication with containers 135a, 135b (shown in FIG. 1) of a wash fluid, such as saline or other solution. Tubings 132a, 132b may include in-line sterile barrier filters 130a, 130b for filtering any particulate from a fluid before it enters the flow path leading to second branched-connector 126 and, ultimately separator 101. In one embodiment, the sterile barrier filters 130a, 130b may be 0.2 μm filters. The wash medium or fluid flows from the wash fluid source through tubing segments 132a, 132b where it is filtered by the sterile barrier filters 130a, 130b described above, and then passes through tubing 128 to the input of the branched-connector 126 described above.

Tubing segment 136 defines a flow path connected at one end to branched-connector 126 and to an inlet port 20 of the separator 101. Preferably, in accordance with the present disclosure, separation device 101 is a spinning membrane separator of the type described in U.S. Pat. Nos. 5,194,145 and 5,053,121, which are incorporated by reference, U.S. Provisional Patent Application Ser. No. 61/451,903 and PCT/US2012/028522, also previously incorporated herein by reference.

As shown in FIG. 3 (and described in detail in connection with FIG. 5), the spinning membrane separator 101 has at least two outlet ports. Outlet 46 of separator 101 receives the waste from the wash (i.e., the diluted suspension medium) and is connected to tubing 138, which defines a flow path to waste product container 140. The waste product container 140 includes a further connection port 141 for sampling or withdrawing the waste from within the product container.

Separation device 101 preferably includes a second outlet 48 that is connected to tubing segment 142 for directing the desired biological cell/fluid product to the in-process container(s) 122 or the product container 150. To permit this, the other end of tubing segment 142 is connected to branched-connector 144, which branches into and defines a flow path to one or more in-process containers 122 and a flow path to a "final" product container 150. The product container 150 may also include a sampling assembly (not shown).

Figure 4:
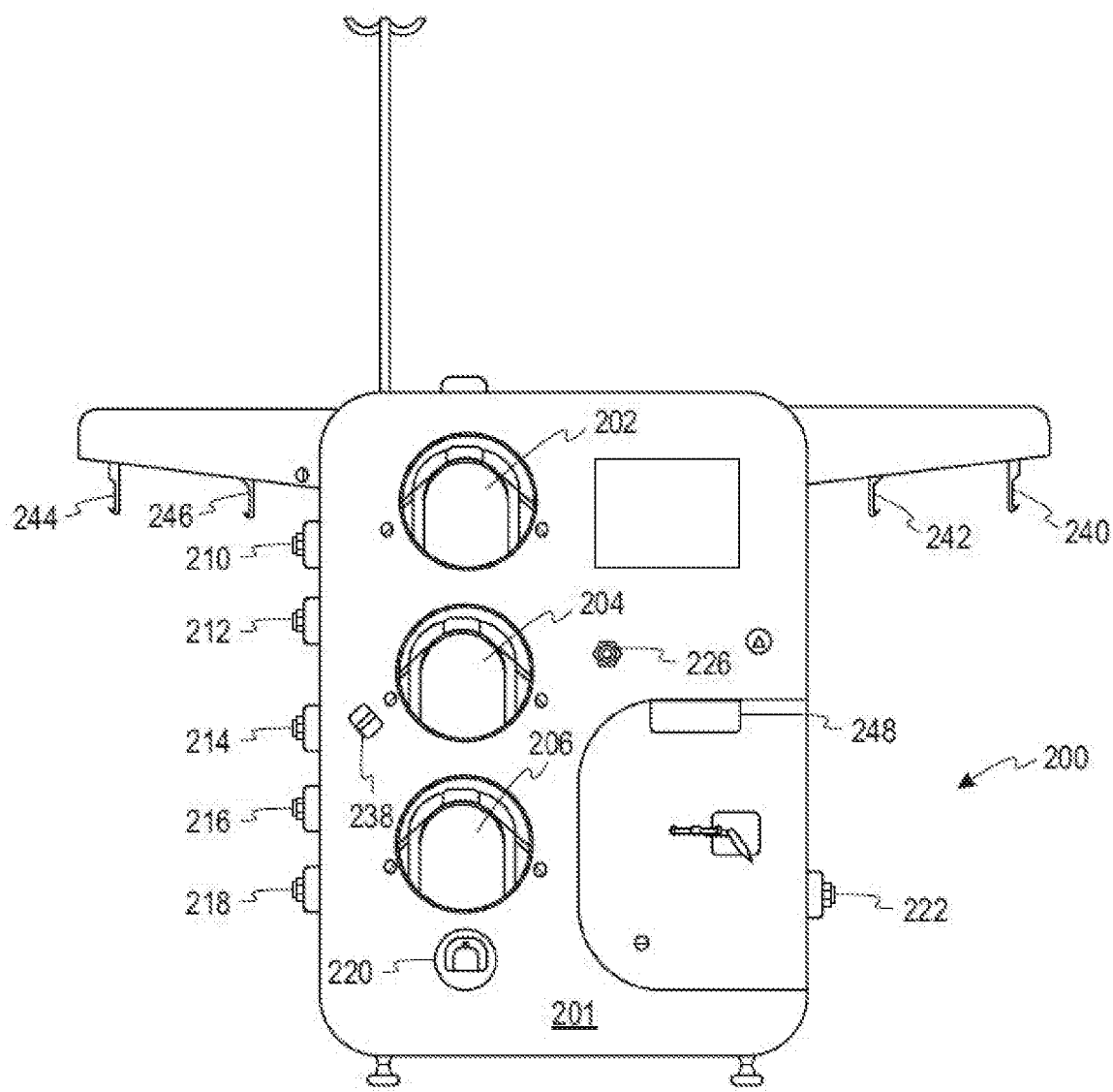
FIG. 4 is a frontal view of the reusable cell processing apparatus.

FIG. 4 shows the front panel 201 of reusable hardware processing apparatus 200, also referred to herein as "hardware". Apparatus 200 may be of compact size suitable for placement on a tabletop of a lab bench and adapted for easy transport. Alternatively, apparatus 200 may be supported by a pedestal that can be wheeled to its desired location. In any event, as shown in FIG. 4, apparatus 200 includes a plurality of peristaltic pumps such as pumps 202, 204 and 206 on front panel 201. Pump segments of the disposable fluid circuit (described above) are selectively associated with peristaltic pumps 202, 204, and 206. The peristaltic pumps articulate with the fluid set of FIG. 3 at the pump segments identified by reference numerals 162, 166, 168 and advance the cell suspension or other fluid within the disposable set, as will be understood by those of skill in the art. Apparatus 200 also includes clamps 210, 212, 214, 216, 218, 220 and 222. The clamps are used to control the flow of the cell suspension through different segments of the disposable set, as described above.

Apparatus 200 also includes several sensors to measure various conditions. The output of the sensors is utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, for example, tubing segment 136), to monitor pressure inside separator 101. Air detector sensor 238 may also be associated with the disposable set 100, as necessary. Air detector 238 is optional and may be provided to detect the location of fluid/air interfaces.

Apparatus 200 includes weight scales 240, 242, 244, and 246 from which the final product container 150, waste container 140, the source container 102 and the in-process container 122, respectively, may depend and be weighed. The weights of the bags are monitored by weight sensors and recorded during a washing or other procedure. Prom measurements of the weight sensors, the device determines whether each container is empty, partially full, or full and controls the components of apparatus 200, such as the peristaltic pumps 202, 204 and 206 and clamps 210, 212, 214, 216, 218, 220 and 222.

Apparatus 200 includes at least one drive unit or "spinner" 248, which causes the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator cause the spinner within the housing of the spinning membrane separator to rotate.

Figure 5:
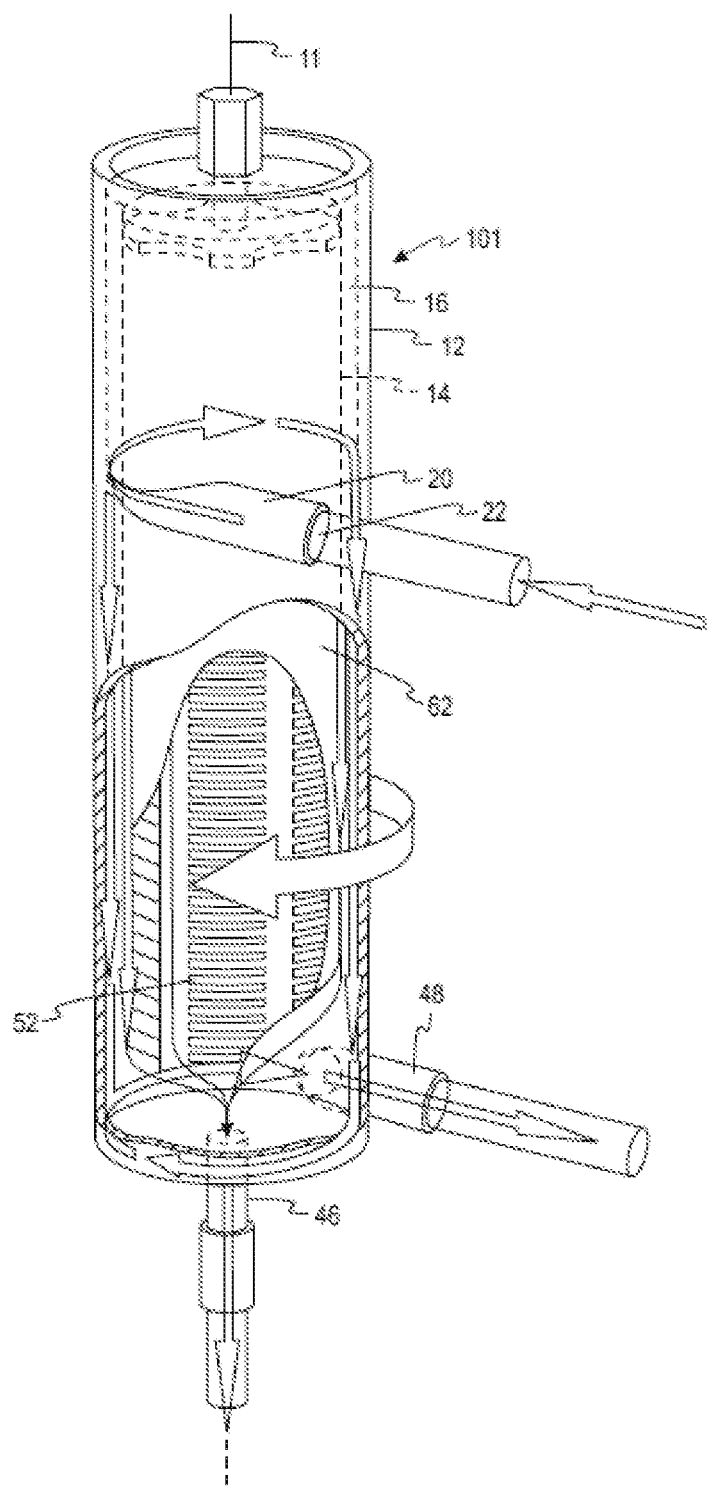
FIG. 5 is a perspective view of a separation/washing device using a spinning membrane.

Turning to FIG. 5, a spinning membrane separation device, generally designated 101, is shown. Such a device 101 forms part of the disposable circuit 100.

Device 101 includes a generally cylindrical housing 12, mounted concentrically about a longitudinal vertical central axis. An internal member 14 is mounted concentric with the central axis 11. Housing 12 and internal member 14 are relatively rotatable. In the preferred embodiment, as illustrated, housing 12 is stationary and internal member 14 is a rotating spinner that is rotatable concentrically within cylindrical housing 12, as shown by the thick arrow in FIG. 5. The boundaries of the flow path are generally defined by gap 16 between the interior surface of housing 12 and the exterior surface of rotary spinner 14. The spacing between the housing and the spinner is sometimes referred to as the shear gap. The shear gap may be approximately 0.02-0.06 inches (0.05-0.15 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example preferably an increasing gap width in the direction. Such a gap width may range from about 0.02 to about 0.075 inches (0.05-0.19 cm). The gap width could be varied by varying the outer diameter of the rotor and/or the inner diameter of the facing housing surface. The gap width could change linearly or stepwise or in some other manner as may be desired. In any event, the width dimension of the gap is preferably selected so that at the desired relative rotational speed, Taylor-Couette flow, such as Taylor vortices, are created in the gap.

Biological fluid is fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48.

Cylindrical housing 12 is completed by a bottom end housing terminating in an outlet orifice 46 concentric with the central axis.

In the illustrated embodiment, the surface of the rotary spinner 14 is at least partially, and is preferably substantially or entirely, covered by a cylindrical porous membrane 62. The membrane 62 may have a nominal pore size between 0.8 and 10 microns (μm), for example. Membranes may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In an embodiment, the nylon membrane may have a pore size of approximately 0.8 μm and a thickness of approximately 150 μm or greater. Membranes of this type will typically retain all cellular components (e.g., red blood cells, white blood cells) and certain formed blood components, e.g., platelets. In another embodiment, the membrane may be made of a thin (approximately 10 μm thick) sheet of unsupported polycarbonate, for example, with a pore size of approximately 4.0 μm. In this embodiment, pores (holes) may be cylindrical and larger than those described above. The pores may be sized to allow small formed components (e.g., platelets, microparticles, etc.) to pass, while the desired cells (e.g., white blood cells and larger red blood cells) are collected.

Having thus described the processor, including disposable circuit 100 and reusable hardware 200, reference is made to FIG. 2 to discuss additional details of the control unit or controller 300. As mentioned above, the controller 300 may include a microprocessor 304 (which, in fact may include multiple physical and/or virtual processors). According to other embodiments, the controller 300 may include one or more electrical circuits designed to carry out the actions described herein. In fact, the controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304, may cause the microprocessors 304 to carry out one or more actions as described below.

As is also illustrated in FIG. 2, the controller 300 may be coupled to one or more of the structures described above, for example to receive information (e.g., in the form of signals) from these structures or to provide commands (e.g., in the form of signals) to these structures to control the operation of the structures. As illustrated, the controller 300 may be coupled to the scales 240, 242, 244, 246, the sensors 226, 238 and the at least one input 302 to receive information from those devices. Additionally, the controller 300 may be coupled to the pumps 202, 204, 206, the clamps 210, 212, 214, 216, 218, 220, 222, and the drive 248 to provide commands to those devices to control their operation. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 that is disposed on the front panel 201 of the device 200, the video display 308 also being coupled to the controller 300. The input could also include a reader or scanner, such as a barcode reader or scanner or an RFID reader. The assembly of the input/touch screen 302 and video display 308 may be one of the aforementioned structures to which the controller 300 is coupled from which the controller 300 receives information and to which the controller 300 provides commands. According to still other embodiments, the input 302 may be in the form of computer equipment that permits the cell processing system including the controller 300 to communicate (whether via wires, cables, etc. or wirelessly) with other cell processing systems over a local network, or with other cell processing systems or other computer equipment (e.g., a server) over local networks, wide area networks, or the Internet. According to such an embodiment, the input may include an internal transmitter/receiver device.

Having discussed the structure of embodiments of the cell processing system disclosed herein, the operation of the cell processing system is now discussed. In this regard, reference is made to U.S. Patent Application Pub. No. US 2013/0092630, the contents of which are incorporated herein by reference, which document discloses methods and systems for washing biological cells using a reusable hardware apparatus and disposable fluid circuit including a spinning membrane separator which may be generally applicable to the cell processing system described herein. The methods disclosed in this document involve the processing of biological cells, such as mononuclear cells for subsequent therapeutic administration.

In general terms, the operator may first activate (e.g., switch on) apparatus 200, at which point the apparatus 200 conducts self-calibration checks, including the checking of the peristaltic pumps 202, 204, 206, clamps 210, 212, 214, 216, 218, 220, 222, and sensors 226, 238. Apparatus 200 may then prompt the user to enter or modify process parameters using the input 302, including by way of example and not by way of limitation the amount of cell suspension to be processed, the number of cycles to take place, etc. The apparatus 200 may then prompt the operator to mount the disposable set 100, after which apparatus 200 automatically checks to determine whether the disposable set 100 is properly installed. Once the set 100 is properly installed, the controller 300 prompts the operator to connect the biological fluid (e.g., 102 of FIG. 3) via a spike connector or sterile connection (e.g., 103, 104 of FIG. 3) and the wash medium (e.g., 135a, 135b of FIG. 3) via a spike connector (e.g., 134a, 134b of FIG. 3). In one embodiment, the biological fluid/cells may be apheresis-collected mononuclear cells, and the wash medium may be a saline solution.

Once the operator confirms that the solutions are connected, the controller 300 primes the disposable set 100. In the embodiment discussed above, the set 100 may be primed with saline, although other biocompatible aqueous solutions may also be used. The controller 300 then commences processing the biological fluid/cells. The biological fluid/cells is/are transferred from source container (e.g., 102 of FIG. 3) through the set to the spinning membrane separator 101 via the operation of one or more peristaltic pumps 202, 204 and 206. In a similar fashion, the wash medium is delivered from its container (e.g., 135a, 135b of FIG. 3) through the set to the spinning membrane separator 101. The biological cells are collected in either an in-process bag (e.g., 122 of FIG. 3) for additional processing or in a product container (e.g., 150 of FIG. 3), while supernatant is separated and removed to waste container (e.g., 140 of FIG. 3). Once the processing is completed, the controller prompts the operator to sample, seal and remove the product container 150.

A specific embodiment of a method 400 of operating the apparatus 200 is provided in FIG. 6. According to this embodiment, the method 400 of operating the apparatus 200 includes several steps, which steps may be grouped or organized into one or more cycles. For example, reduction, rinse and dilution steps 404, 406, 408 may define a first cycle, reduction, rinse, and dilution steps 414, 415, 416, 418 may define an optional intermediate cycle (which cycle may be omitted, or the steps 414, 415, 416 and/or 418 may be repeated several times to define intermediate cycles—e.g., a 6-cycle procedure may involve the performance of some or all of steps 414-418 a total of 4 times), and reduction, rinse, and dilution steps 424, 426, 428 may define a final cycle. It will be recognized that an apparatus 200 need not perform every step illustrated in FIG. 6, but an apparatus 200 may operate as illustrated in FIG. 6 according to this disclosure.

The controller 300 may cause the apparatus 200 to perform the step of priming the set 100 at block 402. According to this step, wash media from the wash media containers 135a, 135b is transferred to the disposable set 100. Wash media may also be transferred to the source container 102. In fact, a small amount of wash media may be transferred to each of the other containers 102, 122, 140, 150 to ensure that the containers are connected 102, 122, 140, 150. To this end, the controller 300 may cause clamps 214, 216, 218, 220, 222 to open to permit the transfer of fluid to the containers 102, 122, 140, 150.

Once the priming is complete at block 402, the method 400 continues to block 404, where the controller 300 causes the apparatus 200 to perform the first cycle reduction step. According to this step, the controller 300 causes the biological fluid from the source container 102 and wash media from the wash media container(s) 135a, 135b to be transferred to the separator 101. For example, the controller 300 may open clamps 214, 212 (and/or 210) and operate pumps 204, 202 to transfer the fluids from the containers 102, 135a (and/or 135b) to the separator 101. The separator 101 (in conjunction with operation of the drive 248 by controller 300) produces two streams: a first, or retentate, stream that is directed into the in-process container 122, and a second, or filtrate, stream that is directed into the waste container 140. For example, the controller 300 may open clamp 218 and operate pump 206 to cause flow into the in-process container 122 (clamp 220 being closed), and may open clamp 222 to permit flow into the container 140. After the step of block 404 is complete, the controller 300 causes wash media to be passed through the set (i.e., the set is rinsed) and the media is added to the in-process bag 122 at block 406. This may be achieved, for example, by closing clamps 214, 222, while leaving clamps 212 (and/or 210), 218 open and operating pumps 202, 206. After block 406, the method 400 proceeds to block 408, where the controller 300 causes additional wash media to be added to the in-process bag 122. When block 408 is complete, the method 400 passes from the first cycle to the intermediate cycle.

At optional block 414, the controller 300 may cause the apparatus 200 to reduce the fluid in the in-process bag 122 further by transferring the fluid to the separator 101 without additional dilution, and passing the supernatant to the waste container 140 while the cells are returned to the in-process bag 122. For example, the controller 300 opens clamps 216, 218, 222 and operates pumps 204, 206 and drive 248. The controller 300 may continue to cause the apparatus 200 to perform this step until certain user-defined limits have been satisfied. It is also possible that the controller 300 may skip this optional step entirely while operating according to the method 400, and proceed instead to step 415.

At optional block 415, the controller 300 may cause the apparatus 200 to operate such that the feed into the separator 101 is maintained at a constant packed cell volume (PCV). Because cells are being processed from the in-process container 122, concentrated, and then directed back to the in-process container 122, the PCV of the in-process container 122 would continuously increase. To limit or prevent the continuous increase, the controller 300 causes the apparatus 200 is add wash media at increasing rates. As such, the controller may open clamp 212 (and/or 210) and clamps 216, 218, 222 while operating pumps 202, 204, 206 and drive 248, for example.

Once block 415 is complete, the controller 300 may cause the apparatus to perform a rinse of the set at block 416 and to add wash media to the in-process bag 122 at block 418. When block 418 is complete, the method 400 passes from the intermediate cycle to the final cycle.

The final cycle begins with block 424, where the controller 300 causes the biological fluid from the in-process container 122 and wash media from the wash media containers 135a, 135b to be transferred to the separator 101. For example, the controller 300 may open clamps 216, 212 (and/or 210) and operate pumps 204, 202 to transfer the fluids from the containers 102, 135a (and/or 135b) to the separator 101. Again, the separator 101 produces two streams: a first, or retentate, stream that is directed into the retentate, or product, container 150 (instead of the in-process container 122), and a second, or filtrate, stream that is directed into the waste container 140. For example, the controller 300 may open clamp 220 and operate pump 206 to cause flow into the product container 150, and may open clamp 222 to permit flow into the container 140. After the step of block 424 is complete, the controller 300 causes wash media to be passed through the set (i.e., the set is rinsed) and the media is added to the product bag 150 at block 426. This may be achieved, for example, by closing clamps 216, 222, while leaving clamps 212 (and/or 210), 220 open and operating pumps 202, 206. After the block 426, the method 400 proceeds to block 428, where the controller 300 causes wash media to be added to the product bag 150. When block 428 is complete, the method 400 may continue with other steps, such as incubation, as are desired before the product bag 150 is sampled, sealed and removed from the apparatus 200.

The systems and methods described herein may be effective, for example, in the washing of cells such as red blood cells and/or white blood cells. In one example of red cell washing, stored red blood cells may be washed to remove accumulated free hemoglobin, spent storage solution, or extracellular components. The washing solution may be sterile docked or otherwise included in the closed system of the disposable processing set of the type described above. The treated cells may then be washed with the washing solution such as saline, Adsol or E-Sol (the latter of which are red blood cell storage solutions and generally comprise dextrose, mannitol and a buffer) to reconstitute the red blood cells for subsequent storage and transfusion.

While the foregoing discussion references embodiments in the form of a cell processing system, other systems may incorporate this technology as well. These systems may share the technical challenges faced by the aforementioned cell processing system, and incorporation of the technology may provide similar advantages. For example, a separation system, more particularly a filtration system, or even more particularly a microfiltration system, also may include a processor to receive a fluid to be processed and a controller. Further, certain embodiments of such a processor may include a disposable fluid circuit (which circuit may include a membrane used for filtration) and reusable hardware, and the controller may be configured to operate the processor.

Having thus described the structure and operation of embodiments of a cell processing system that may be used with the filling options discussed herein, the filling options now are discussed in detail.

Several embodiments of different fill options are illustrated in FIGS. 7-28. According to these embodiments, a filling system distributes a product, for example disposed in a product container 150 received from the system 100, to a plurality of other containers, for storage, shipment or both after the processing of the biological fluid. In fact, it may be possible to fill a plurality of containers from one or more such product containers using such a fill option, where the volume of the individual containers being filled are smaller, even many times smaller, than the volume of the product container(s). According to certain embodiments, the volume of the individual containers to be filled may be at least an order of magnitude smaller than the volume of the product container (which may be referred to as a source container with respect to the fill options, because fluid is being pumped from the container).

To this end, the source container (which will be referred to herein as the container 150, to indicate that it may be the same container as the product container 150 referred to above according to certain embodiments) may be connected to a new circuit or set, which set is used with a pump to distribute the product from container 150 to one or more additional containers. The processor 200 (and in particular, the controller 300) may be in communication with the filling system, and data may be transmitted back and forth between the processor 200 and the filling system or may be shared between the processor 200 and the filling system. In fact, the filling system may have its own controller (as illustrated, which controller may include a microprocessor, other circuits or circuitry and one or more memories, which may be one or more tangible non-transitory computer readable memories, with computer executable instructions by which the microprocessor is programmed and which when executed by the microprocessor may cause the microprocessor to carry out one or more actions being stored on the memory/memories) that is in communication with the controller 300.

First with reference to FIG. 7, an embodiment of a filling system 500 is illustrated. The filling system 500 includes a pump 502 (which may be in the form of a peristaltic pump) and one or more filling stations 504. Each of the filling stations 504 may include a sensor 506 (e.g., a fluid detector), a valve (e.g., in the form of a clamp that defines a pinch valve) 508, and a container 510 (such as a rigid or semi-rigid walled container with a vent according to certain embodiments). Each filling station 504 may also include a scale (not illustrated) to determine the weight (and thus the volume) of product in the container 510. While three filling stations 504 are illustrated in FIG. 7, it will be appreciated that additional filling stations may be added to the left of the leftmost filling station 504 illustrated.

Each of the filling stations 504 may be connected to the container 150 by a transfer set 520. The transfer set 520 is connected at a first end to the container 150 (e.g., via a port of the container 150, which may be sterile welded to the transfer set) and at a second end to the filling stations 504, while the region intermediate to the first and second ends is disposed in the pump 502. Additional tubing may connect the sensor 506, clamp 508 and container 510. According to certain embodiments, such as the embodiment illustrated, a common manifold 522 is used to connect the individual filling stations 504 to the container 150.

The filling stations 504 may include additional equipment as well. For example, each filling station may include a substation for forming a sterile connection between the tubing of the filling station 504 and the container 510, and for disconnecting the container 510 from the transfer set 520. Such a sterile connection/seal substation may include a mechanism that connects or disconnects the ends of the tubing of the filling station 504 and the container 510 without exposing the interior of the tubing to ambient contamination. The filling system 500 may include a single sterile connection substation for all of the associated filling stations 504, or each filling station 504 may include its own sterile connection substation.

The filling system 500 also includes a controller 530 and a pressure sensor 532. As mentioned above, the controller 530 may include a microprocessor, other circuits or circuitry and one or more memories, which may be one or ore tangible non-transitory computer readable memories, with computer executable instructions by which the microprocessor is programmed and which when executed by the microprocessor may cause the microprocessor to carry out one or more actions being stored on the memory/memories. The controller 530 may be coupled to the pump 502 and the sensor 532, as well as to the sensors 506 and clamps 508.

In operation, the controller 530 causes the clamp 508 associated with one of the filling stations 504 to open. As a consequence, fluid may now flow from the container 150 to the container 510. The controller 530 then causes the pump 502 to operate to draw fluid from the container 150 in the direction of the arrow below the manifold 522. At the same, the controller 530 monitors the pressure sensor 532 to detect a spike in the pressure of the fluid in the transfer set 520. The controller 530 may also monitor the fluid sensor 506 and the scale associated with the container 510 (if included). A spike in the pressure of the fluid in the transfer set 520 is indicative of the container 510 (which has a semi-rigid wall) being full. At this point, the controller 530 causes the pump 502 to cease operation, and causes the clamp 508 to be closed. The controller 530 then may proceed to repeat the steps of the method with the next filling station 504 along the transfer set 520.

Figure 8:
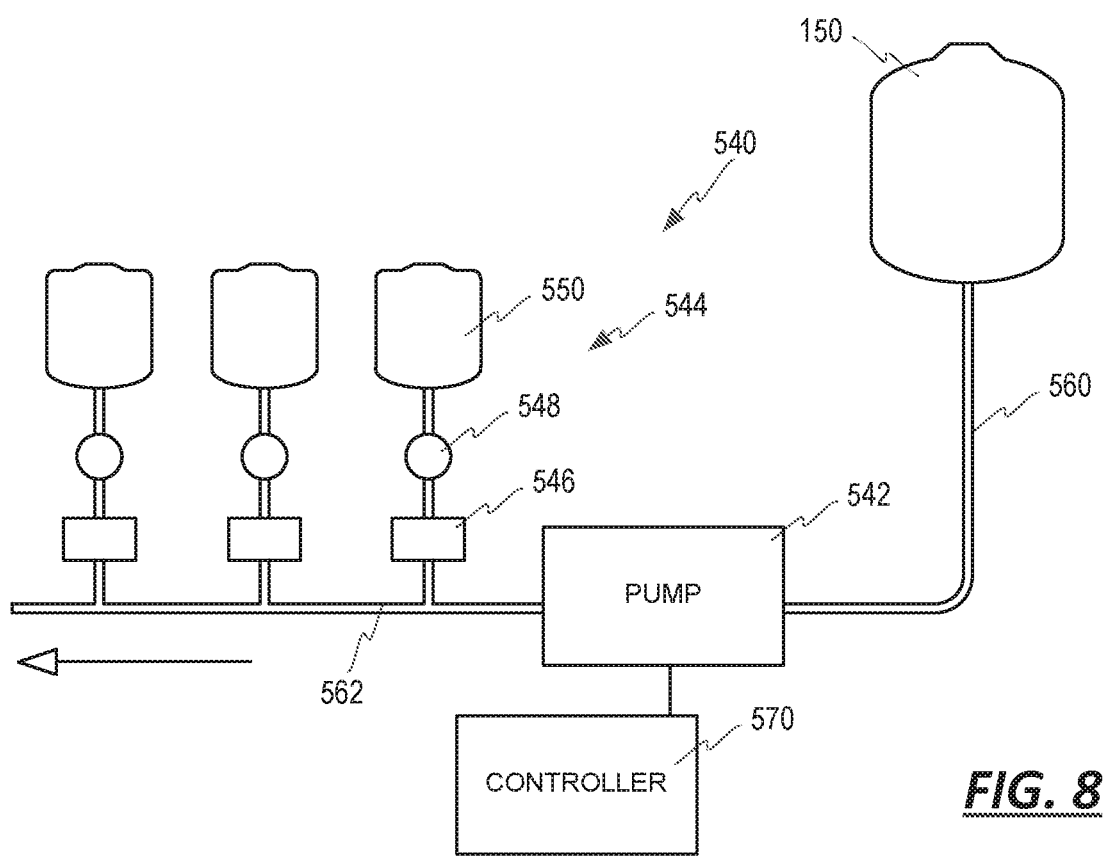
FIG. 8 is a schematic diagram of another embodiment of a filling system for use with a product container, such as may be produced in accordance with the embodiment of FIGS. 1-6.

FIG. 8 illustrates another filling system 540. The filling system 540 includes a pump 542 in the form of a syringe pump, and one or more filling stations 544. Each of the filling stations 544 may include a sensor 546 (e.g., a fluid detector), a valve (e.g., in the form of a clamp that defines a pinch valve) 548, and a container 550 (such as a flexible walled bag). Each filling station 544 may also include a scale (not illustrated) to determine the weight (and thus the volume) of product in the container 550. While three filling stations 544 again are illustrated in FIG. 8, it will be appreciated that additional filling stations may be added to the left of the leftmost filling station 544 illustrated.

Each of the filling stations 504 may be connected to the container 150 by a transfer set 560. The transfer set 560 is connected at a first end to the container 150 (e.g., via a port of the container 150, which may be sterile welded to the transfer set) and at a second end to the filling stations 544, while the region intermediate to the first and second ends is connected to the pump 542. Additional tubing may connect the sensor 546, clamp 548 and container 550. According to certain embodiments, such as the embodiment illustrated, a common manifold 562 is used to connect the individual filling stations 544 to the container 150.

As was the case with the filling stations 504, the filling stations 544 may include additional equipment as well. For example, each filling station may include a substation for forming a sterile connection between the tubing of the filling station 544 and the container 550, and for disconnecting the container 550 from the transfer set 560.

The filling system 540 also includes a controller 570. The controller 570 also may include a microprocessor, other circuits or circuitry and one or more memories, which may be one or more tangible non-transitory computer readable memories, with computer executable instructions by which the microprocessor is programmed and which when executed by the microprocessor may cause the microprocessor to carry out one or more actions being stored on the memory/memories. The controller 570 may be coupled to the pump 542, as well as to the sensors 546 and clamps 548.

In operation, the controller 570 causes the clamp 548 associated with one of the filling stations 544 to open. As a consequence, fluid may now flow from the container 150 to the container 550. The controller 570 then causes the syringe pump 542 to operate to draw fluid from the container 150, and then to pump the fluid in the direction of the arrow below the manifold 562. The controller 570 is programmed to operate the syringe pump 542 so as to provide a constant volume of fluid to each of the filling stations 544. To this end, the pressure sensor 532 is not required, but the controller 570 may need to be programmed to vary the amount of fluid pumped to each of the filling stations 544 to correct for variances caused by the length of the tubing/manifold 562 between the pump 542 and the individual filling stations 544. The controller 530 may also monitor the fluid sensor 546 and the scale associated with the container 550 (if included). Once the fluid has been pumped, the controller 570 causes the pump 542 to cease operation, and causes the clamp 548 to be closed. The controller 570 then proceeds to repeat the steps of the method with the next filling station 544 along the transfer set 560.

Figure 9:
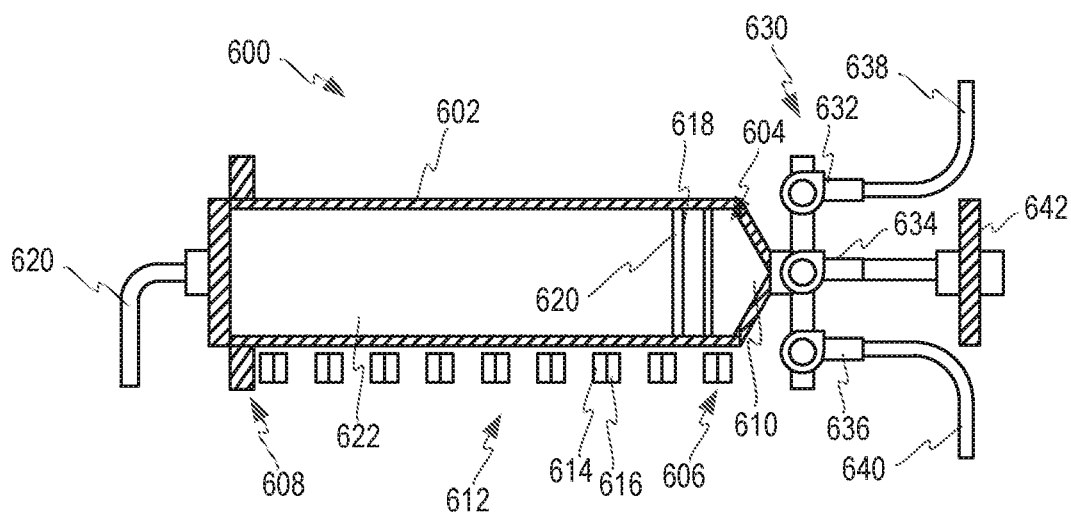
FIG. 9 is a cross-sectional view of a syringe pump as may be used with the embodiment of the filling system illustrated in FIG. 8, with a plunger head assembly in a first position.
Figure 10:
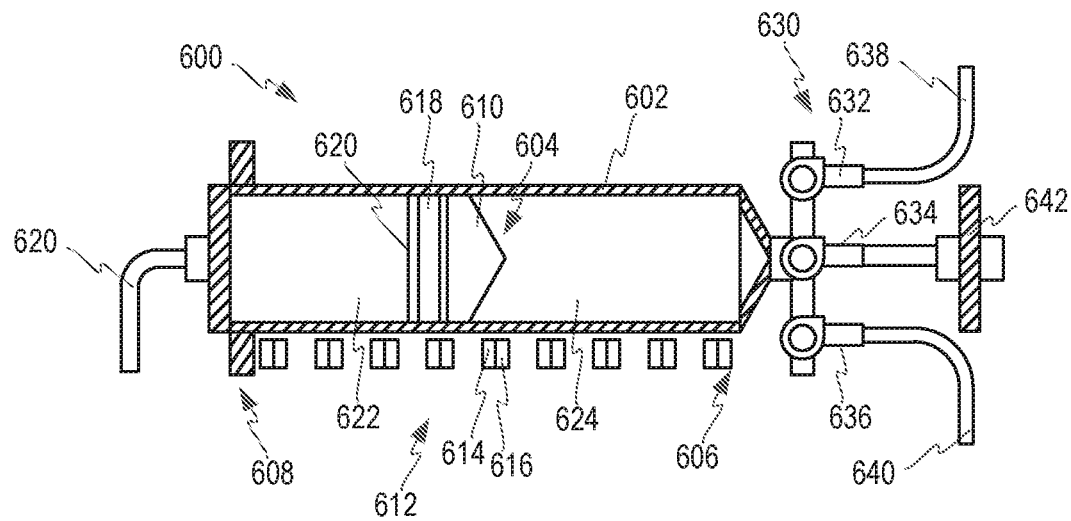
FIG. 10 is a cross-sectional view of the syringe pump of FIG. 9, with a plunger head assembly in a second position.
Figure 11:
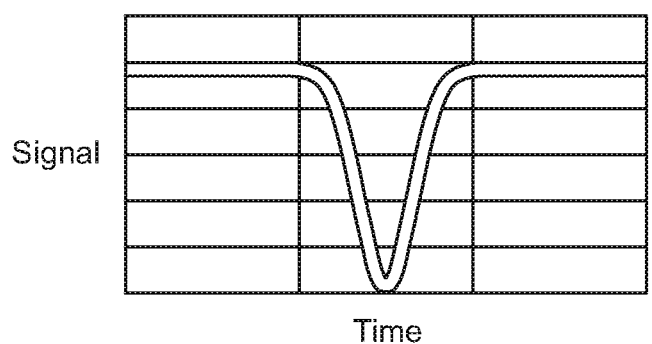
FIG. 11 is a chart of the signal response of one of the infrared detectors or sensors of the syringe pump of FIG. 10.

FIGS. 9 and 10 illustrate an embodiment of a syringe pump 600 that may be used with the embodiment of FIG. 8 as the pump 542. The syringe pump 600 of FIGS. 9 and 10 includes a syringe barrel 602 and a piston or plunger head assembly 604. The plunger head assembly 604 is moveable (translatable) between a first end 606 and a second end 608 of the barrel 602.

The plunger head assembly 604 includes the plunger 610 and a one part of a position detector 612. According to the illustrated embodiment, the position detector 612 includes a plurality of transmitter/sensor pairs 614, 616. According to the illustrated embodiment, the transmitters (or emitters) 614 may be in the form of infrared light emitting diodes, and the sensors 616 may be in the form of infrared sensors. The transmitter/sensor pairs 614, 616 are disposed along the length of the barrel 602 between the first end 606 and the second end 608. The pairs 614, 616 operate in conjunction with an infrared reflector 618 that is part of the plunger head assembly 604. As one example, the reflector 618 may be in the form of a reflective strip that is disposed about the perimeter of a rigid disc 620 that is attached opposite the plunger 610.

In operation, the position detector 612 (which would be coupled to the controller 570) would use the interaction between the transmitter/sensor pairs 614, 616 and the reflector 618 to determine the positon of the plunger head assembly 604 along the barrel 602. In particular, light emitted from the transmitter 614 would be received by the sensor 616 (or would be received over a threshold amount) if the light contacts the reflector 618. Otherwise, the light would not be received by the sensor 616 (or would not be received below the threshold amount). Depending on the amount of light received by the sensor 616, a signal generated by the sensor 616 would vary (see, e.g., FIG. 11). Depending on the signals received from the individual transmitter/sensor pairs 614, 616, the controller 570 may determine the position of the plunger head assembly 604 along the barrel 602 between the first and second ends 606, 608.

A vacuum/pressure source is attached via line (e.g. tubing) 620 to the end 608 of the barrel 602. The end 608 is otherwise closed, forming a first variable volume space 622 between the closed end 608 of the barrel 602 and the plunger head assembly 604. Filtered air may be pumped into and out of the space 622 to move the plunger head assembly 604 between the first and second ends 606, 608 of the barrel 602. The movement of the plunger head assembly 604 causes a second variable volume space 624 between the plunger head assembly 604 and the first end 606. Compare FIGS. 9 and 10. Fluid from the container 150 may be drawn and ejected from the space 624 according to the movement of the plunger head assembly 604.

A set 630 of three valves 632, 634, 636 is attached to the end 606 of the barrel 602. The set of valves 630 is coupled to the controller 570; the set 630 may be coupled as a group, or as individual valves 632, 634, 636. The valves 632, 636 connect the barrel 602 to the container 150 through line (e.g., tubing) 638, and to the container 550 through line (e.g., tubing) 640. The valve 634 connects the barrel 602 to a filtered vent 642 to permit the barrel 602 to vent to atmosphere, for example.

In operation, the syringe head assembly 604 starts at a first position, such as is illustrated in FIG. 9. The controller 570 opens the valve 632 and causes the vacuum/pressure source to operate, and draw vacuum behind the plunger head assembly 604 (i.e., space 622). As a consequence, the plunger head assembly 604 moves in the direction of the end 608 (i.e., from the end 606 to the end 608) and draws fluid from the container 150 via the line 638 into the space 624 (see FIG. 10). The controller 570 then closes valve 632, opens valve 636 and operates the vacuum/pressure source to pump pressurized air into the space 622. This causes the plunger head assembly 604 to move in the direction of the end 606 (i.e., from the end 608 to the end 606) and push fluid to the container 550 via the line 640 from the space 624.

To limit the fluid remaining in the barrel 602, the controller 570 may close the valve 636, open the valve 634 and cause the vacuum/pressure source to operate to draw vacuum behind the plunger head assembly 604. As a consequence, air is drawn through the filtered vent 642 into the space 624. The controller 570 then closes the valve 634, opens the valve 636, and causes the vacuum pressure source to operate to pump pressurized air into the space 622. This causes the plunger head assembly 604 to again move in the direction of the end 606 and push any remaining fluid to the container 550 via the line 640.

Figure 12:
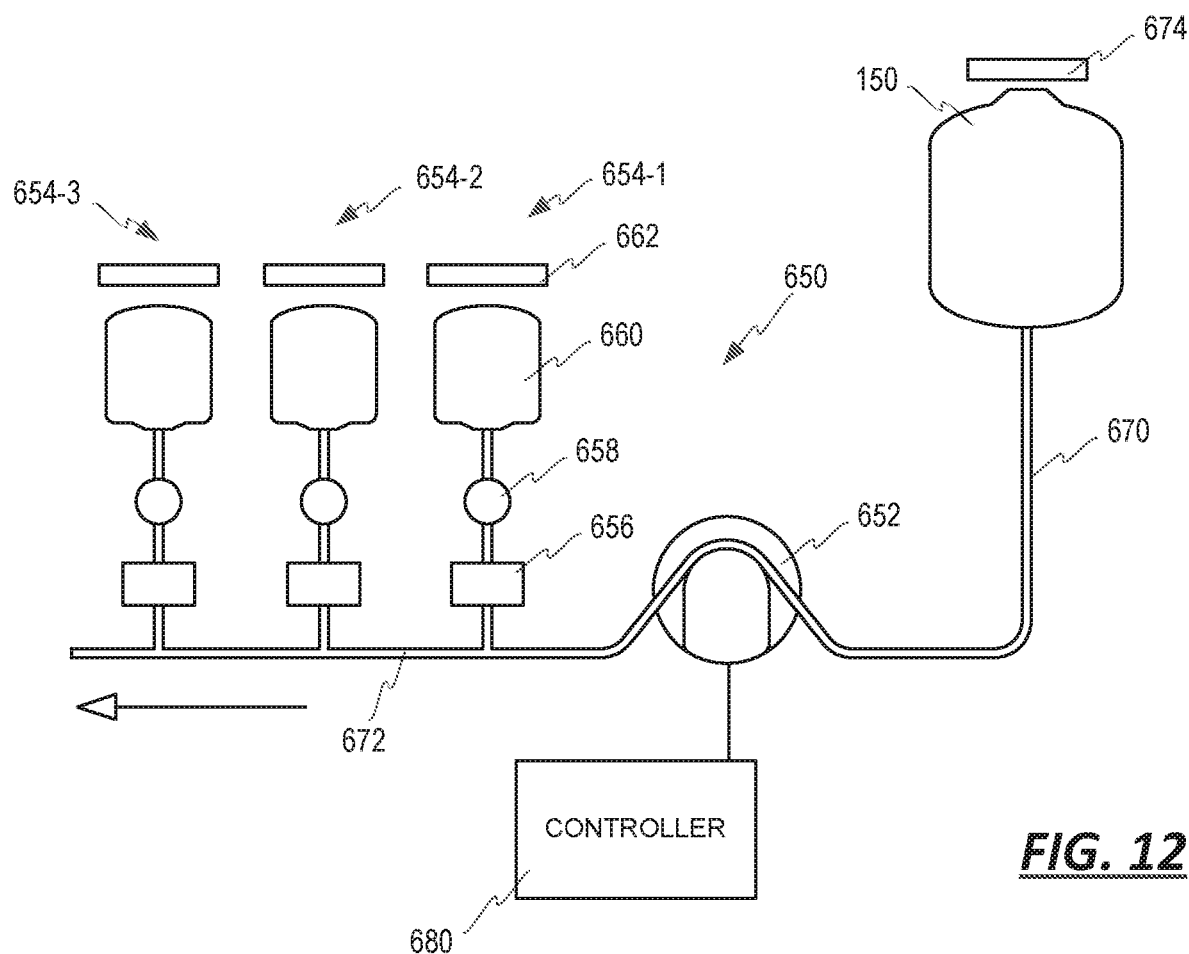
FIG. 12 is a schematic diagram of another embodiment of a filling system for use with a product container, such as may be produced in accordance with the embodiment of FIGS. 1-6.

FIG. 12 illustrates a further filling system 650. The filling system 650 includes a pump 652 in the form of a continuous pump (e.g., a peristaltic pump or a bi-directional peristaltic pump), and one or more filling stations 654-1, 654-2, 654-3. Each of the filling stations 654-1, 654-2, 654-3 may include a sensor 656 (e.g., a fluid detector), a valve (e.g., in the form of a clamp that defines a pinch valve) 658, and a container 660 (such as a flexible walled bag). Each filling station 654-1, 654-2, 654-3 may also include a scale 662 to determine the weight (and thus the amount) of product in the container 660. While three filling stations 654-1, 654-2, 654-3 again are illustrated in FIG. 12, it will be appreciated that additional filling stations may be added to the left of the leftmost filling station 654-3 illustrated.

Each of the filling stations 654-1, 654-2, 654-3 may be connected to the container 150 by a transfer set 670. The transfer set 670 is connected at a first end to the container 150 (e.g., via a port of the container 150, which may be sterile welded to the transfer set) and at a second end to the filling stations 654-1, 654-2, 654-3, while the region intermediate to the first and second ends is disposed in the pump 652. Additional tubing may connect the sensor 656, clamp 658 and container 660. According to certain embodiments, such as the embodiment illustrated, a common manifold 672 is used to connect the individual filling stations 654-1, 654-2, 654-3 to the container 150.

As was the case with the other filling stations mentioned above, the filling stations 654-1, 654-2, 654-3 may include additional equipment as well. For example, each filling station may include a substation for forming a sterile connection between the tubing of the filling station 654-1, 654-2, 654-3 and the container 660, and for disconnecting the container 660 from the transfer set 670.

The filling system 650 also includes a controller 680. The controller 680 also may include a microprocessor, other circuits or circuitry and one or more memories, which may be one or more tangible non-transitory computer readable memories, with computer executable instructions by which the microprocessor is programmed and which when executed by the microprocessor may cause the microprocessor to carry out one or more actions being stored on the memory/memories. The controller 680 may be coupled to the pump 652, as well as to the sensors 656 and clamps 658.

Figure 13:
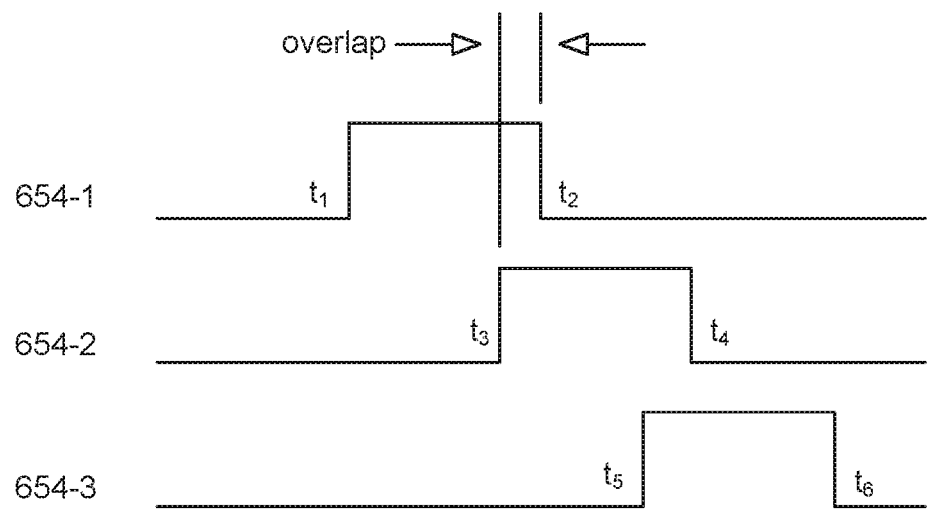
FIG. 13 is a timing diagram for the opening and closing of the clamps associated with each of the containers in the embodiment illustrated in FIG. 12.

In operation, the system 650 may operate as illustrated in FIG. 13. According to this embodiment, each container 660 is not filled independently from the container 150 as was done in the embodiments of illustrated in FIGS. 7 and 8. Instead, the clamps 658 of the individual filling stations 654-1, 654-2, 654-3 are opened and closed such that there is an overlap between the time a container 660 associated with a first filling station 654-1 is filled from the container 150 and the time a container 660 associated with a second filling station 654-2 is filled, and so on. In particular, the embodiment illustrated in FIG. 13 includes three filling stations 654-1, 654-2, 654-3, although it will be recognized that more than three stations may be associated with a filling system according to other embodiments.

As illustrated in FIG. 13, the clamp 658 associated with a first filling station 654-1 is opened at time $t_1$ and closed at time $t_2$. Between time $t_1$ and $t_2$, fluid is being pumped into the container 660 associated with the first filling station 654-1. In a similar fashion, the clamp 658 associated with a second filling station 654-2 is opened at time $t_3$ and closed at time $t_4$, and the clamp 658 associated with a third filling station 654-3 is opened at time $t_5$ and closed at time $t_6$. As such, fluid is being directed into the containers 660 associated with the first and second filling stations 654-1, 654-2 between times $t_3$ and $t_2$, and associated with the second and third filling stations 654-2, 654-3 between times $t_5$ and $t_4$. While the times are referred to as start and end times, it will be recognized that according to certain embodiments, the system 650 may cycle through all of the stations 654-1, 654-2, etc. multiple times until the container 150 is exhausted (see below); as such, the start and end times may refer to a particular cycle in a plurality of cycles, rather than the start and end time for the completion of filling of a particular container 660.

It is believed that by providing an overlap in the start and end times for the filling of the individual containers limits or prevents the pressure from changing rapidly, keeping the system in equilibrium. It is also believed that the time-controlled distribution not only improves volume consistency, but also concentration uniformity.

The filling system 650 may be operated according to a second method as well, which method may be combined with the foregoing method described in relation to FIG. 13. According this method, the containers 660 may be filled in "round robin" fashion. This embodiment of method of operation utilizes the scales 662 at each filling station 654-1, 654-2, 654-3, as well as a scale 674 for the container 150. All of the scales 662, 674 are coupled to the controller 680.

According to the "round robin" method of operation, each of the containers 660 associated with filling stations 654-1, 654-2, 654-3 would be filled with the same volume of fluid from the container 150 in each round. The user may be permitted to select the flow rate at which fluid is transferred from the container 150 to the containers 660, as well as the volume of fluid to be transferred from the container 150 to each of the containers 660 in each round. The scales 662 may be utilized by the controller 680 as part of a feedback loop (with the pump 652) to control the volume pumped into each container 660.

It will be recognized that after the fluid has been transferred or pumped from the container 150 to the containers 660, some air may remain in each of the containers 660. To remove the air in each of the containers 660, the pump may be operated in reverse, to pump the air remaining in each bag after transfer back to the container 150. Once the air purge is complete, each of the bags may be heat sealed and removed from the transfer set 670. Additional transfer sets 670 may be connected to the container 150 to process additional volume, if necessary.

Figure 14:
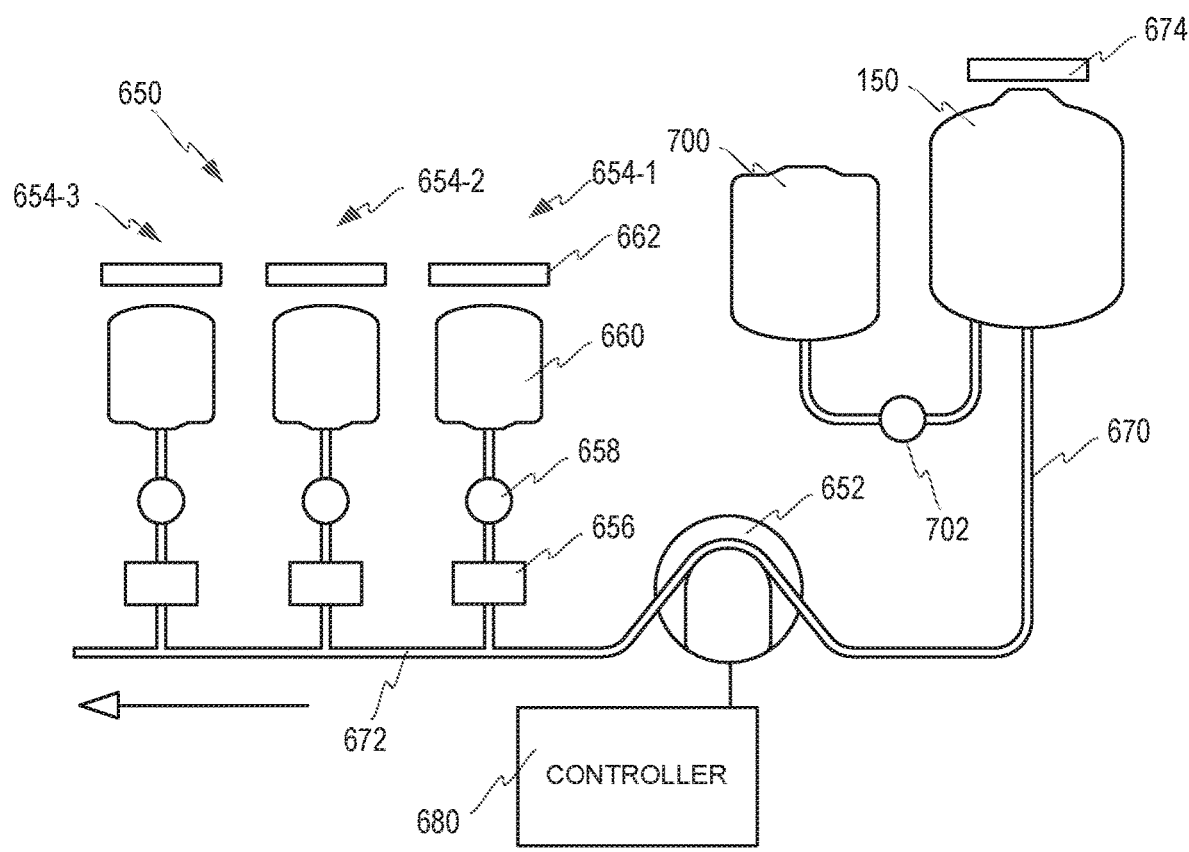
FIG. 14 is a schematic diagram of a further embodiment of a filling system, similar to that of illustrated in FIG. 7, with an air bag that may be selectively placed in fluid connection with the product container to ensure that the contents of the product container have been expelled.

A further variant is possible relative to any of the systems illustrated in FIGS. 7, 8, 12 (or the following embodiments), and is illustrated in FIG. 14. In particular, the embodiment of FIG. 14 is illustrated with respect to the embodiment of FIG. 12. In addition to the equipment previously described, a container 700 filled with a gas (e.g., air) is provided in selective fluid communication with container 150 via a clamp 702. The clamp 702 is closed during normal operation. The clamp 702 is opened to permit the gas (e.g., air) from the container 700 to be pumped into the container 150 to limit or prevent the contents of the container 150 from remaining in the container 150. For example, the air may be moved manually (by compressing the container 700), or a pump may be provided to transfer the air from the container 700 to the container 150. Such a variant may be used with the embodiments below as well.

A second set of fill options are provided in FIGS. 15-19. Unlike the fill options illustrated in FIGS. 7-14, the fill options of FIGS. 15-19 do not have an individual valve associated with each container at each filling station. Instead, the embodiments of FIGS. 15-19 have a single valve assembly that is associated with all of the containers.

Figure 15:
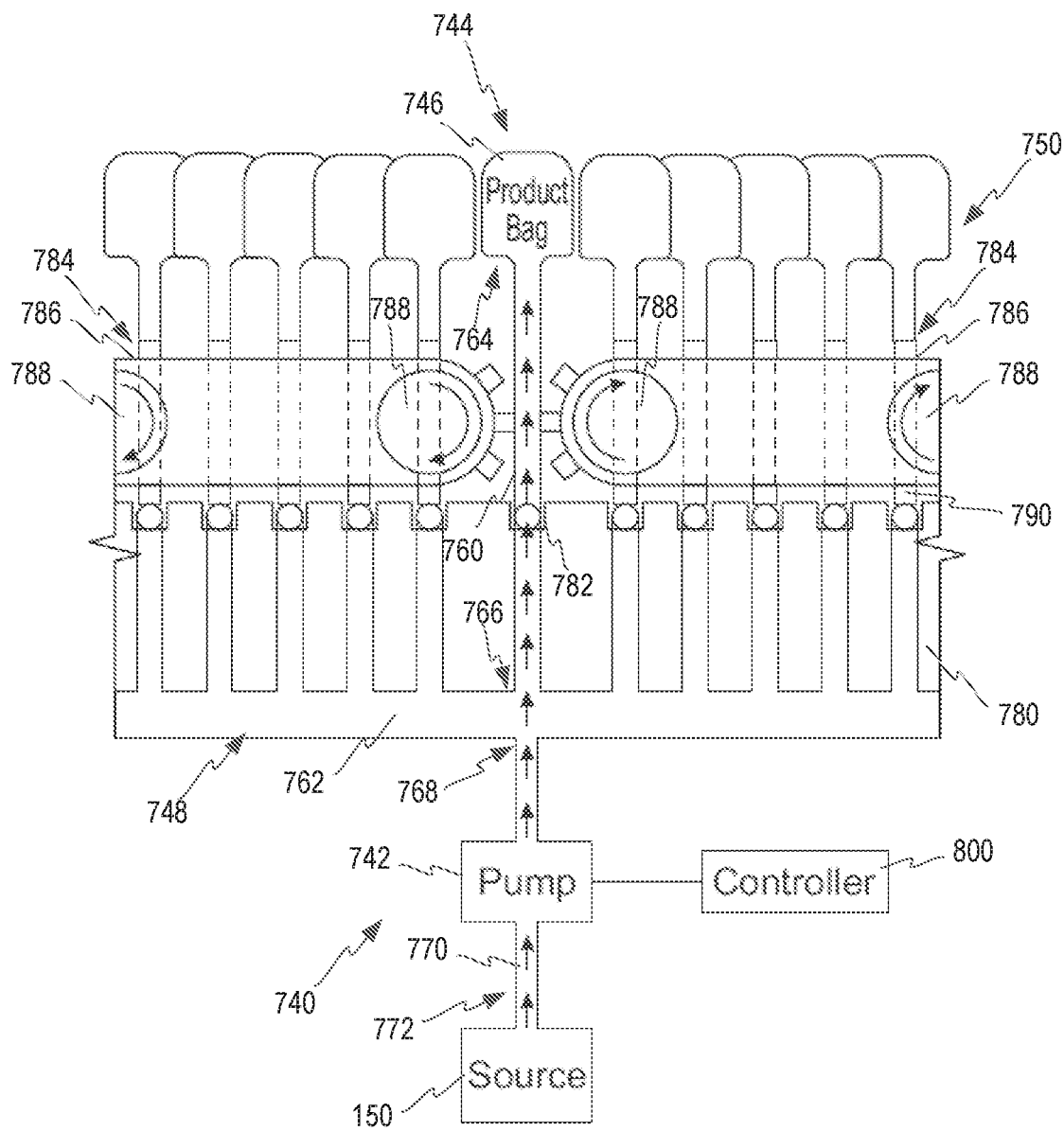
FIG. 15 is a schematic diagram of another embodiment of a filling system for use with a product container, such as may be produced in accordance with the embodiment of FIGS. 1-6.

Thus, according to an embodiment illustrated in FIG. 15, the filling system 740 includes a pump 742 (e.g., a syringe pump), and one or more filling stations 744. Each of the filling stations 744 includes a container 746 that is in connection with the container 150 via a transfer set 748. While a large number of filling stations 744 are illustrated, the number of filling stations 744 in a particular embodiment may be greater or lesser than the number illustrated in FIG. 15. A valve assembly 750 cooperates with the transfer set 748 to selectively open and close fluid flow paths between the container 150 and the containers 746.

As illustrated, the transfer set 748 includes a plurality of individual lines (e.g., tubing) 760 that are connected to a common manifold 762. The lines 760 may be sterile welded or otherwise joined at a first end 764 to the container 746 and at a second end 766 to the manifold 762. The manifold 762, in turn, may be sterile welded of otherwise joined to a first end 768 of a line 770, a second end 772 of the line 770 being sterile welded or otherwise joined to the container 150.

The valve assembly 750 includes table 780 with a plurality of notches, grooves or insets 782 to accept the lines 760 of the transfer set 748, each of the notches 782 each sized to accept one of the lines 760 of the transfer set 748. The mechanism 750 also includes a pair of surfaces 784, each in the form of a continuous, elongated track or band 786 that may be supported between opposing wheels 788. The surfaces 784 and the notches 782 cooperate to compress the lines 760 (i.e., the surfaces 784 are disposed against the lines 760 immobilized in the notches 782) to limit or prevent fluid flow between the container 150 and the containers 746. In fact, the surfaces 784 may include one or more protrusions 790 that depend into the notches 782 to compress the lines 760.

The surfaces 784 are spaced from each other such that they do not cooperate with every line 760. Instead, at least one line 760 is exposed between the surfaces 784, such that the surfaces 784 are not in contact with the line 760 to compress the line 760, thereby limiting or preventing fluid flow along the line 760. As such, the container 746 associated with the uncompressed line 760 is in fluid communication with the container 150 via the line 770 that is disposed in or attached to the pump 742. As such, operation of the pump 742 causes fluid to flow from the container 150 to the container 746 via the lines 760, 770 and the manifold 762.

The system 740 also includes a controller 800 (similar to the controllers mentioned above) that is coupled to the pump 742 and the valve assembly 750. The controller 800 operates the pump 742 to move fluid from the container 150 to one (or more) of the containers 746 in accordance with the fluid flow path(s) available as a consequence of the operation of the valve assembly 750. The controller 800 also operates the valve assembly 750 to change the individual line 760 that is uncompressed, and thus the container 746 that is in fluid communication with the container 150. To this end, one or both of the table 780 and the surfaces 784 may have a motor associated therewith that causes the table 780 to move relative to the surfaces 784. For example, a linear actuator may be attached to the table 780, such that movement of the table 780 to the left or right causes the individual notch 782 aligned with the space between the surfaces 784 to vary. The linear actuator may be coupled to the controller 800, and the controller 800 may operate the actuator to cause this relative motion.

Thus, in operation, the controller 800 causes the actuator to move the table 780 to the right or to the left, so as to expose one of the lines 760 between the surfaces 784. The controller 800 then operates the pump 742 to transfer fluid from the container 150 to the container 746. Once the controller 800 determines that the desired amount of fluid has been transferred from the container 150 to the container 746 (e.g., see the mechanisms for making this determination as outlined above relative to the embodiments of FIGS. 7-14), the controller 800 causes the actuator to move the table to the right or to the left, so as to compress the line 760 associated with the container 746 just filled and to expose the line 760 associated with an unfilled container 746 of another of the filling stations 744.

Figure 16:
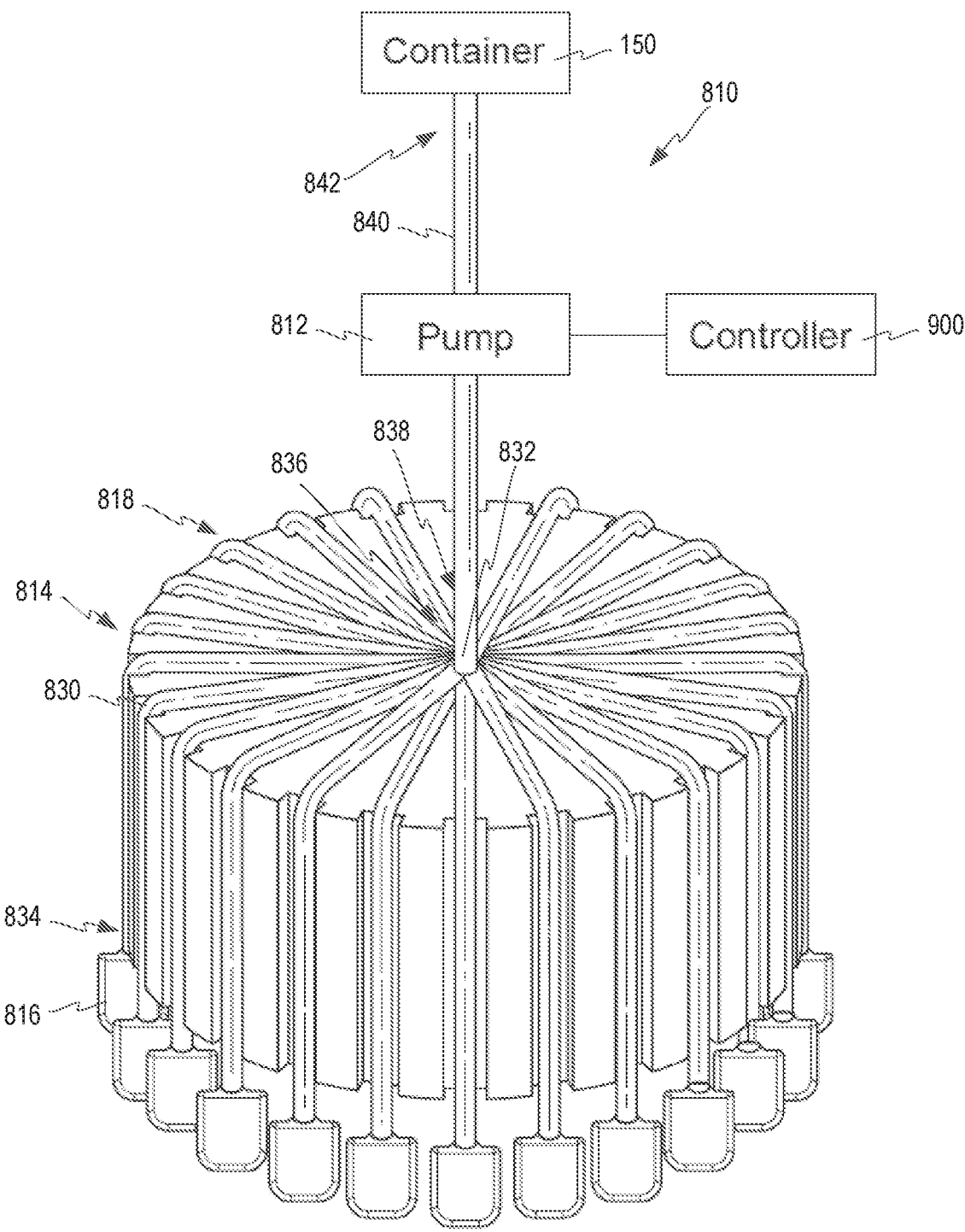
FIG. 16 is a schematic diagram of yet another embodiment of a filling system for use with a product container, such as may be produced in accordance with the embodiment of FIGS. 1-6.
Figure 17:
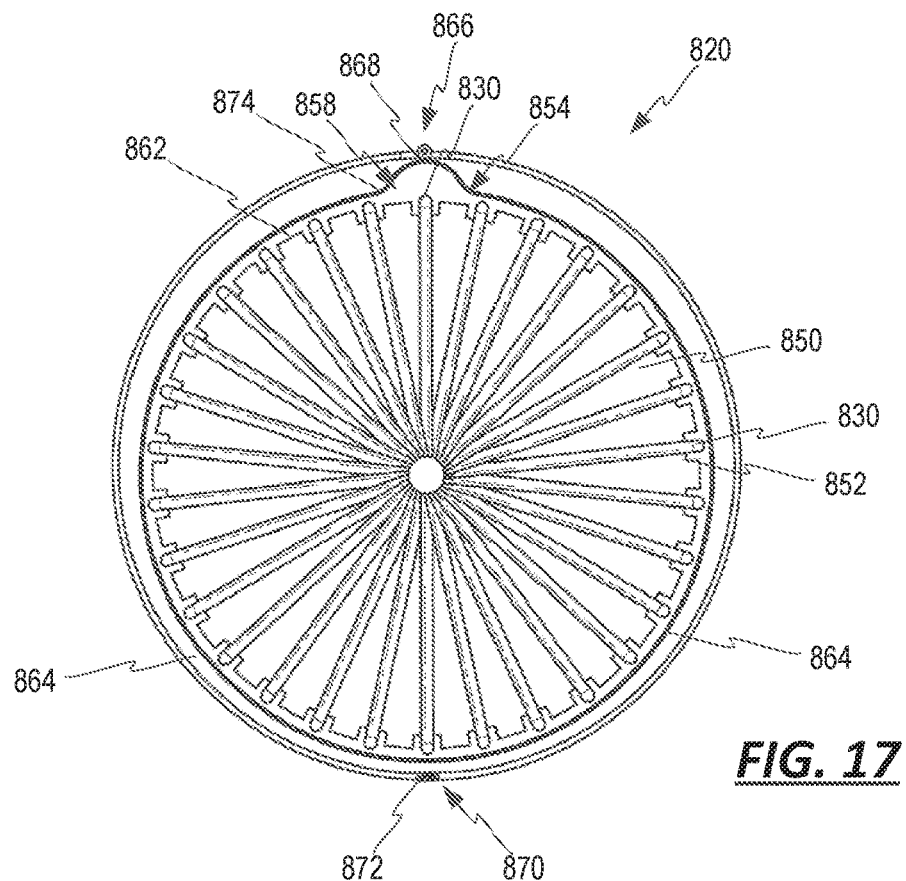
FIG. 17 is a schematic diagram of an embodiment of an indexing system that may be used with the embodiment of FIG. 16.
Figure 18:
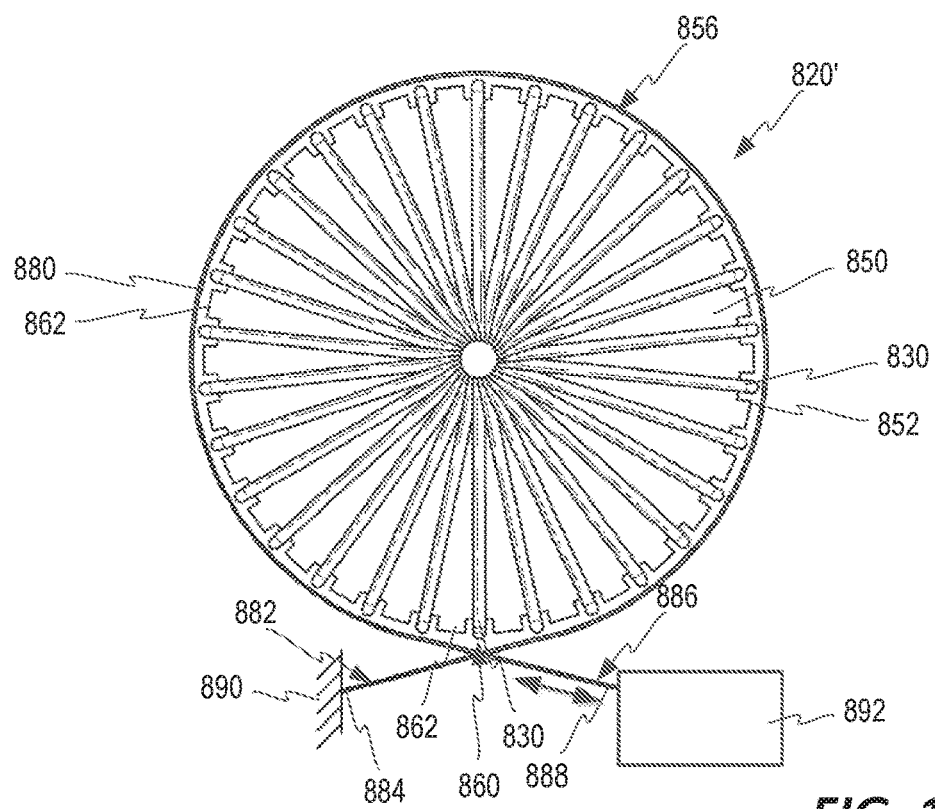
FIG. 18 is a schematic diagram of another embodiment of an indexing system that may be used with the embodiment of FIG. 16.

According to another embodiment illustrated in FIGS. 16-18, a filling system 810 includes a pump 812 (e.g., peristaltic pump, a bi-directional peristaltic pump, or a syringe pump), and one or more filling stations 814. See FIG. 16. Each of the filling stations 814 includes a container 816 that is in connection with the container 150 via a transfer set 818. While a large number of filling stations 814 are illustrated, the number of filling stations 814 in a particular embodiment may be greater or lesser than the number illustrated in FIG. 16. A valve assembly 820, 820' (see FIGS.

17 and 18) cooperates with the transfer set 818 to selectively open and close fluid flow paths between the container 150 and the containers 816.

As illustrated in FIG. 16, the transfer set 818 includes a plurality of individual lines (e.g., tubing) 830 that are connected to a common hub 832. The lines 830 may be sterile welded or otherwise joined at a first end 834 to the container 816 and at a second end 836 to the hub 832. The hub 832, in turn, may be sterile welded of otherwise joined to a first end 838 of a line 840, a second end 842 of the line 840 being sterile welded or otherwise joined to the container 150.

FIGS. 17 and 18 illustrate two different embodiments of a valve assembly 820, 820'. Each embodiment includes oval or circular table (or disc) 850 with a plurality of notches, grooves or insets 852, each of the notches 852 each sized to accept one of the lines 830 of the transfer set 818. The valve assembly 820, 820' also includes surfaces 854, 856 (see FIGS. 17 and 18, respectively), defined by a continuous, band that is disposed about the table 850. The surfaces 854, 856 and the notches 852 cooperate to compress the lines 830 to limit or prevent fluid flow between the container 150 and the containers 816.

The surfaces 854, 856 each have a region 858, 860 where the surface 854, 856 is spaced from a surface 862 of the table 850 such that the surfaces 854, 856 do not cooperate with every line 830. Instead, at least one line 830 is exposed between the surfaces 854, 862 or 856, 862, such that the surfaces 854, 856 are not in contact with the line 830 to compress the line 830, thereby limiting or preventing fluid flow along the line 830. As such, the container 816 associated with the uncompressed line 830 is in fluid communication with the container 150 via the line 840 that is disposed in the pump 812. As such, operation of the pump 812 causes fluid to flow from the container 150 to the container 816 via the lines 830, 840 and the hub 832.

As illustrated in FIG. 17, the surface 854 is defined as the inner surface of a pair of arcuate or c-shaped half-clamps 864 that are connected a first end 866 by a hinge 868 and a second end 870 by a fastener 872. The fastener 872 (which may be in the form of a quick connect or snap-fit closure) is secured to place the surface 854 into cooperation with the lines 830, except one, to compress the lines 830 and prevent fluid flow through the lines 830. The fastener 872 may be opened or closed; for example, the fastener 872 may be opened to permit a transfer set 818 to be placed or removed.

To permit one of the lines 830 to be uncompressed by the surface 854, one or both of the half-clamps 864 include a notch or part of a notch 874, such that the notch 874 faces one of the notches 852 at at least one position about the perimeter (or circumference) of the table 850. At this position (approximately 12 o'clock in the illustration of FIG. 17), the line 830 remains uncompressed such that fluid may flow through the line 830.

As illustrated in FIG. 18, the surface 856 is defined by a band or cord 880 that is attached at a first end 882 by a first fastener 884 and at a second end 886 by a second fastener 888. The first and/or the second fastener 884, 888 may attach the end 882 or the end 886 to a fixed structure; alternatively, the first and/or second fastener 884, 888 may attach the end 882 or 886 to a motor or linear actuator. As illustrated, the first fastener 884 attaches the end 882 to a fixed structure 890 and the second fastener 888 attaches the end 886 to a motor or a linear actuator 892. The tension on the band 880 may be adjusted through the operation of the actuator 892; for example, the tension may be loosened to permit a transfer set 818 to be placed or removed.

The band 880 is disposed about the surface 852 of the table 850 (and according to certain embodiments the table 850 may have a track or groove formed in the surface 852 in which the band 880 is disposed) such that an inner surface 894 of the band is in contact with the lines 830 to compress the lines 830 to limit or prevent fluid flow through the lines 830. The band 880 crosses or intersects at at least one position about the perimeter (or circumference) of the table 850 to permit a line 830 at that one positon to remain uncompressed, and there by to permit fluid flow through this line 830. At this position (approximately 6 o'clock in the illustration of FIG. 18), the line 830 remains uncompressed such that fluid may flow through the line 830.

The system 810 also includes a controller 900 (similar to the controllers mentioned above) that is coupled to the pump 812 and may be coupled to the valve assembly 820, 820'. The controller 900 operates the pump 812 to move fluid from the container 150 to one (or more) of the containers 816 in accordance with the fluid flow path(s) available as a consequence of the operation of the valve assembly 820, 820'. The controller 900 also operates the valve assembly 820, 820' to change the individual line 830 that is uncompressed, and thus the container 816 that is in fluid communication with the container 150. To this end, the table 850 may have a motor (e.g., a stepper motor) associated therewith that causes the table 850 to move (rotate) relative to the surface 854, 856. For example, a motor may be attached to the table 850, such that rotation of the table 850 to the clockwise or counterclockwise causes the individual notch 852 to be aligned with notch 874 or the area of intersection of the band 880. The motor may be coupled to the controller 900, and the controller 900 may operate the motor to cause this relative motion.

Thus, in operation, the controller 900 causes the motor to move the table 850 clockwise or counterclockwise, so as to expose one of the lines 830. The controller 900 then operates the pump 812 to transfer fluid from the container 150 to the container 816. Once the controller 900 determines that the desired amount of fluid has been transferred from the container 150 to the container 816 (e.g., see the mechanisms for making this determination as outlined above relative to the embodiments of FIGS. 7-14), the controller 900 causes the motor to move the table 850 clockwise or counterclockwise, so as to compress the line 830 associated with the container 816 just filled and to expose the line 830 associated with an unfilled container 816 of another of the filling stations 814.

Figure 19:
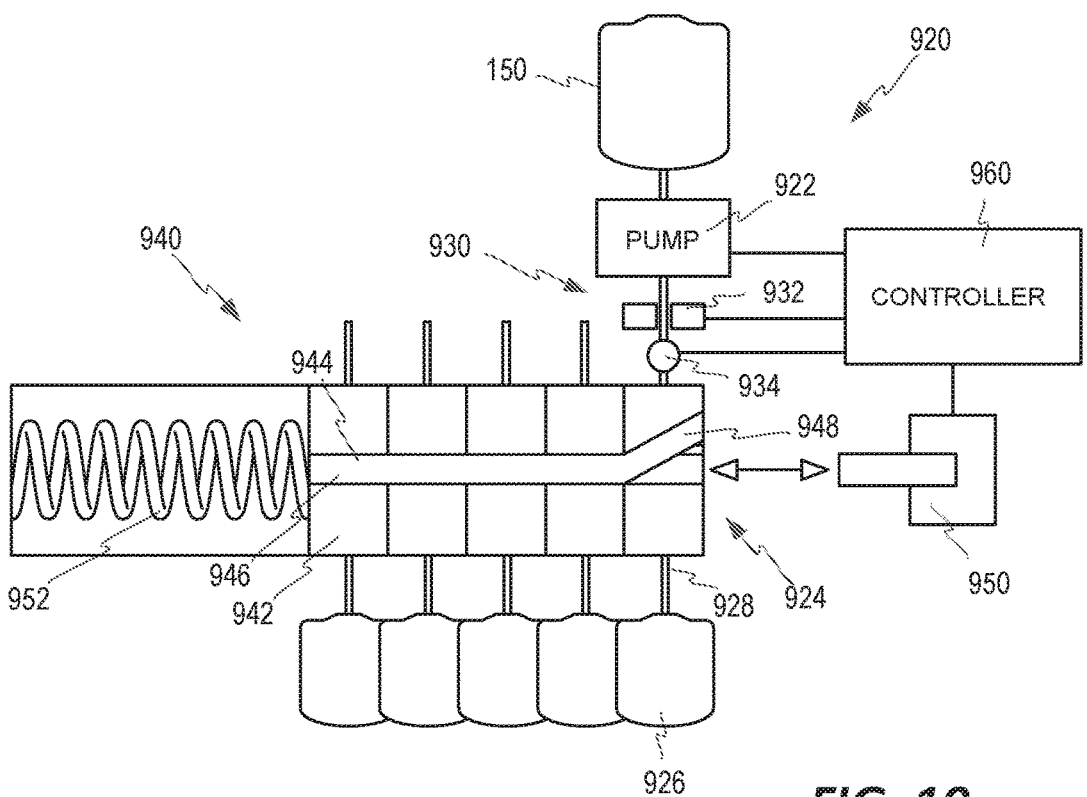
FIG. 19 is a schematic diagram of a further embodiment of a filling system for use with a product container, such as may be produced in accordance with the embodiment of FIGS. 1-6.

A still further embodiment of a filling system 920 is illustrated in FIG. 19. According to this embodiment, the filling system 920 includes a pump 922 (e.g., peristaltic pump, a bi-directional peristaltic pump, or a syringe pump), and one or more filling stations 924. Each of the filling stations 924 includes a container 926 that is in connection with the container 150 via a transfer set 928. While a large number of filling stations 924 are illustrated, the number of filling stations 924 in a particular embodiment may be greater or lesser than the number illustrated in FIG. 19. A valve assembly 930 cooperates with the transfer set 928 to selectively open and close fluid flow paths between the container 150 and the containers 926.

According to this embodiment, the individual containers 926 are individually connected to the container 150 as the individual containers 926 are indexed past the pump 922. When the transfer set 928 of a particular container 926 is aligned with the output of the pump 922, a sterile welder or other sealing valve assembly 932 forms a connection between the output of the pump 922 and the transfer set 928 permitting flow between the container 150 and the container 926. Once the container 150 is filled, which may be determined through the use of a sensor 934 (e.g., an air detector or sensor), the sterile welder 932 forms a seal between the output of the pump 922 and the transfer set 928, limiting or preventing fluid flow between the container 150 and the container 926.

To move from one filling station 924 to the next, an indexer 940 may be used with each of the filling stations 924, each of which may include a block 942 with an aperture 944 therethrough. The aperture 944 accepts a guide 946, which is linear as illustrated but which may have other shapes (e.g., curved) according to other embodiments. The guide 946 has a clamp 948 at one end, which clamp 948 has an open state or a closed state according to the operation of an actuator 950. When the actuator 950 is in contact with the clamp 948, the clamp 948 remains in a closed state; when the actuator 950 is moved out of contact (spaced from) the clamp 948, the clamp 948 is in the open position. When the clamp 948 is in the open position, the blocks 942 move along the guide 946 under the force exerted on the blocks 942 by a spring 952 (although other mechanisms, such as a hydraulic piston or air bag may be substituted for the spring 952), and eventually exit the guide 946 at the end with the clamp 948.

The system 920 also includes a controller 960 (similar to the controllers mentioned above) that is coupled to the pump 922 and the indexer 940 (in particular, the actuator 950), as well as other equipment (such as the welder/sealer 932 and the sensor 934). The controller 960 operates the pump 922 to move fluid from the container 150 to one (or more) of the containers 926 in accordance with the fluid flow path(s) available as a consequence of the operation of the indexer 940. The controller 960 also operates the actuator 950 to change the individual filling station 944 that is aligned with the output of the pump 922, and thus the container 926 that is in fluid communication with the container 150.

Thus, in operation, the controller 960 causes the actuator 950 to move a filling station 924 to the right, so as to align the associated transfer set 928 with the output of the pump 922. The welder 932 forms a connection between the output of the pump 922 and the transfer set 928. The controller 960 then operates the pump 922 to transfer fluid from the container 150 to the container 926. Once the controller 960 determines that the desired amount of fluid has been transferred from the container 150 to the container 926 (e.g., through use of the sensor 932), the controller 960 causes the heat sealer 932 to seal the transfer set 928, and the actuator 950 to move out of cooperation with the clamp 948, so that the next filling station 924 associated with the filled container 926 moves off the end of the guide 946, and the filling station 924 is moved into alignment with the output of the pump 922 by the force of the spring 952.

A third set of embodiments of filling option are illustrated in FIGS. 20-28. According to this set of embodiments, one or more syringes are filled from a product container, the syringes may be intended for storage, shipment, and ultimately use. The syringes may be referred to as prefilled syringes, in that there is no need to fill the syringes from another container at the time of use. According to this set of embodiments, there is no need for a pump disposed between the container 150 and the container intended for use, because the syringe functions both as the use container and the pump.

Figure 20:
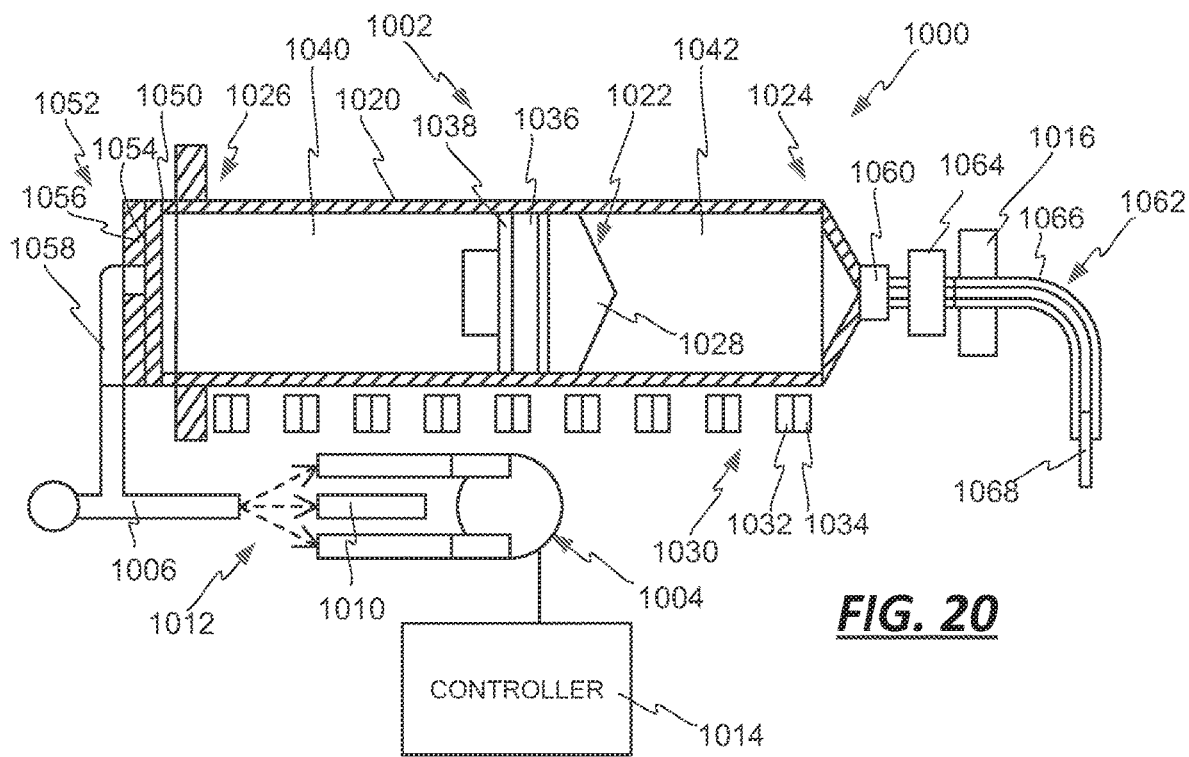
FIG. 20 is a partial schematic diagram of another embodiment of a filling system for producing a pre-filled syringe, which embodiment may be used with a product container such as may be produced in accordance with the embodiment of FIGS. 1-6.
Figure 21:
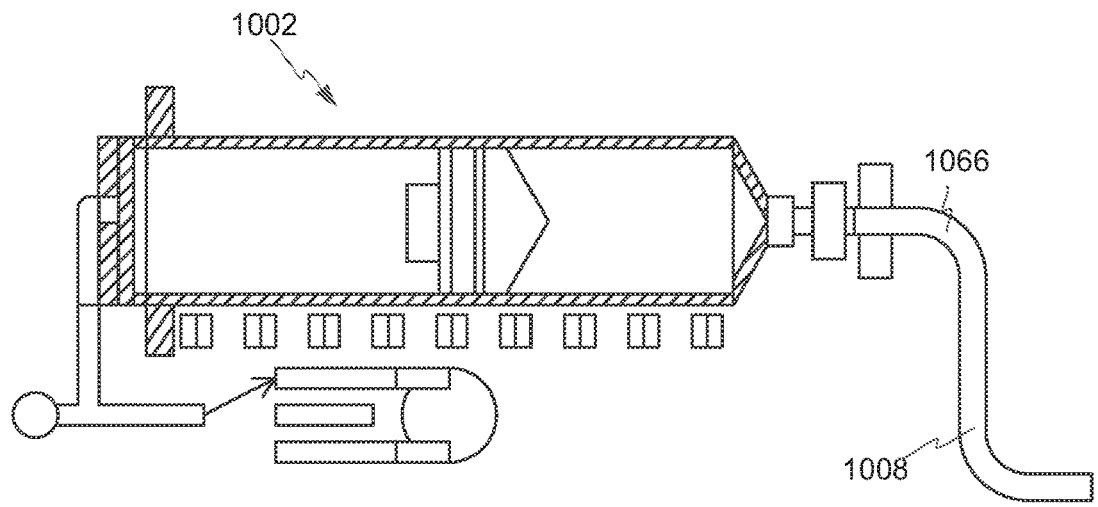
FIGS. 21-26 are partial schematic diagrams of different operational states or positions of the embodiment of FIG. 20.

FIG. 20 illustrates a filling system 1000. The filling system includes the syringe 1002, a vacuum/pressure pump 1004, a line (e.g. tubing) 1006 that connects the pump 1004 to one end of the syringe 1002, a line (e.g. tubing) 1008 that connects the syringe 1002 to the container 150 (see FIG. 21), a vent 1010, and a valve assembly 1012 (which may include one or more valves) to selectively connect the line 1006 to the pump 1004 and the vent 1010. The filling system 1000 also includes a controller 1014, which controller 1014 is coupled to the pump 1004 and may be coupled to other elements (such as a sensor 1016, for example an air or fluid sensor and the valve assembly 1012) as well, as explained in detail below. The pump 1004 and the controller 1014 may be associated with a plurality of syringes 1002, of which one is illustrated in FIGS. 20-26. While the syringe is illustrated as horizontal in FIGS. 20-26, the syringe may be vertically oriented in actual operation of the system 1000, as noted below.

The syringe 1002 includes a syringe barrel 1020 (which may be made of cyclic olefin copolymer, or other materials such as may be inert, optically clear and, for certain applications, liquid-nitrogen compatible) and a piston or plunger head assembly 1022. The plunger head assembly 1022 is moveable (translatable) between a first end 1024 of the barrel 1020 and a second end 1026 of the barrel 1020. The plunger head assembly 1022 includes the plunger 1028 and a one part of a position detector 1030. According to the illustrated embodiment, the position detector 1030 includes a plurality of transmitter/sensor pairs 1032, 1034. According to the illustrated embodiment, the transmitters (or emitters) 1032 may be in the form of infrared light emitting diodes, and the sensors 1034 may be in the form of infrared sensors. The transmitter/sensor pairs 1032, 1034 are disposed along the length of the barrel 1022 between the first end 1024 and the second end 1026. The pairs 1032, 1034 operate in conjunction with an infrared reflector 1036 that is part of the plunger head assembly 1022. As one example, the reflector 1036 may be in the form of a reflective strip that is disposed about the perimeter of a rigid disc 1038 that is attached opposite the plunger 1028. The disc 1038 may also assist in maintaining the coaxial alignment of the plunger assembly 1022 within the barrel 1020.

In operation, the position detector 1030 (which would be coupled to the controller 1014) would use the interaction between the transmitter/sensor pairs 1032, 1034 and the reflector 1036 to determine the positon of the plunger head assembly 1022 along the barrel 1020. In particular, light emitted from the transmitter 1032 would be received by the sensor 1034 (or would be received over a threshold amount) if the light contacts the reflector 1036. Otherwise, the light would not be received by the sensor 1034 (or would not be received below the threshold amount). Depending on the amount of light received by the sensor 1034, a signal generated by the sensor 1034 would vary (see, e.g., FIG. 11). Depending on the signals received from the individual transmitter/sensor pairs 1032, 1034, the controller 1014 may determine the position of the plunger head assembly 1022 along the barrel 1020 between the first and second ends 1024, 1026.

As mentioned above, the pump 1004 is attached via line 1006 to the syringe 1002, and more particularly to the end 1026 of the barrel 1020. The end 1026 is otherwise closed, forming a first variable volume space 1040 between the closed end 1026 of the barrel 1020 and the plunger head assembly 1022. Filtered air may be pumped into and out of the space 1040 to move the plunger head assembly 1022 between the first and second ends 1024, 1026 of the barrel 1020. The movement of the plunger head assembly 1022 causes a second variable volume space 1042 between the plunger head assembly 1022 and the first end 1024. Fluid from the container 150 may be drawn into the space 1042 according to the movement of the plunger head assembly 1022.

The syringe 1002 may include a threaded aperture (as may be defined by a threaded portion of the barrel 1020, for example) 1050 at the second end 1026. A filter assembly 1052 may be attached to the second end 1026 at the threaded aperture 1050. The filter assembly 1052 may include a threaded attachment 1054, which permits the filter assembly 1052 to be threadably attached to the threaded aperture 1050, a filter 1056, and a connector 1058 for connection with to line 1006. According to one embodiment, the filter 1056 is a 0.2 μm polytetrafluoroethylene (PTFE) hydrophobic sterile filter. The connector 1058 may be a female luer slip, for example. The filter assembly 1052 closes the end 1026 of the barrel 1020 and filters the air passing into the space 1040.

The syringe 1002 may also include a male luer-lock tip 1060, Attached to the tip 1060 is an assembly 1062 that permits the syringe 1002 to be connected to the container 150. The assembly 1062 includes a female luer-lock connector 1064 that may be connected to the male luer-lock tip 1060, a section of weldable tubing 1066 connected at a first end to the connector 1064, and a sealing plug 1068 received within a second end of the weldable tubing 1066.

In operation, the system 1000 may perform an integrity check on the syringe as illustrated in FIG. 20. The controller 1014 operates the pump 1004 to pump pressurized air into space 1040. The controller 1014 determines if the position detector 1030 indicates that the position of the plunger head assembly 1022 has moved. The controller 1014 may also determine if other sensors, such as a pressure sensor, indicate that the pressure of the air in the space 1040 has changed. If the controller 1014 determines that the plunger head assembly 1022 has not moved and that the pressure in the space 1040 has not changed, the system 1000 may begin a method to fill the syringe 1002.

The method begins with the attachment of the tubing 1066 to the container 150, such by sterile welding tubing 1008, 1066. See FIG. 21. The controller 1014 then operates the pump 1004 to move the plunger assembly 1022 to the end 1024 of the barrel 1020, by pumping air into the space 1040. See FIG. 22. This may be referred to as the home position. Air in the space 1042 is transferred to the container 150, or at least to the tubing 1008, 1066.

Figure 22:
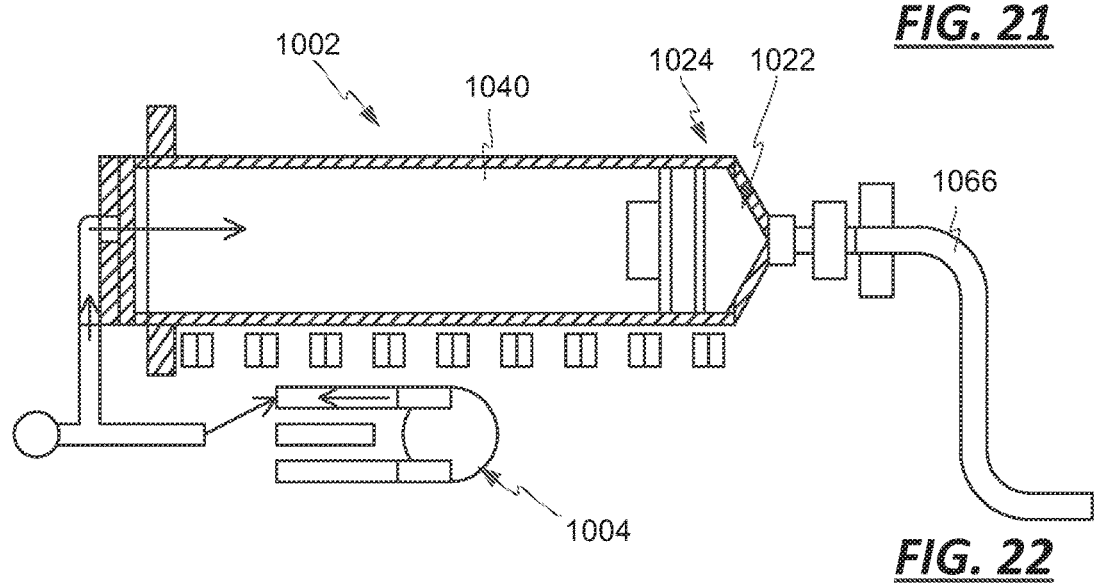
Figure 23:
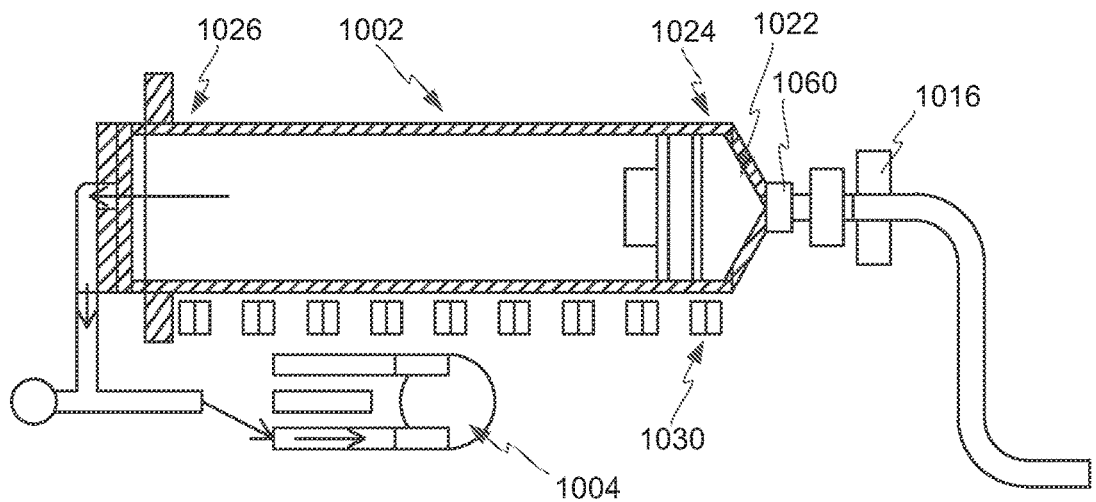
Figure 24:
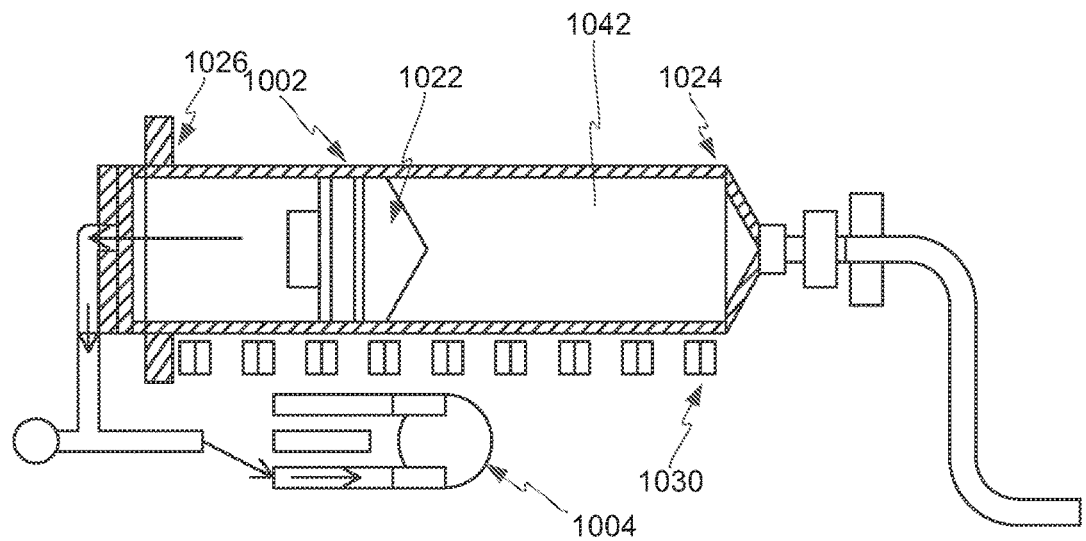
Figure 25:
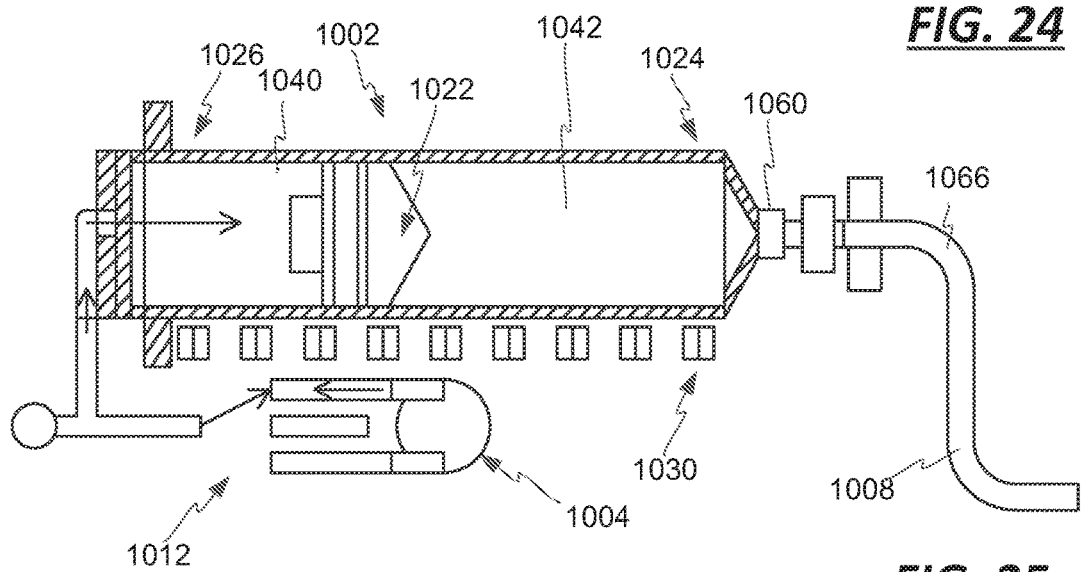
Figure 26:
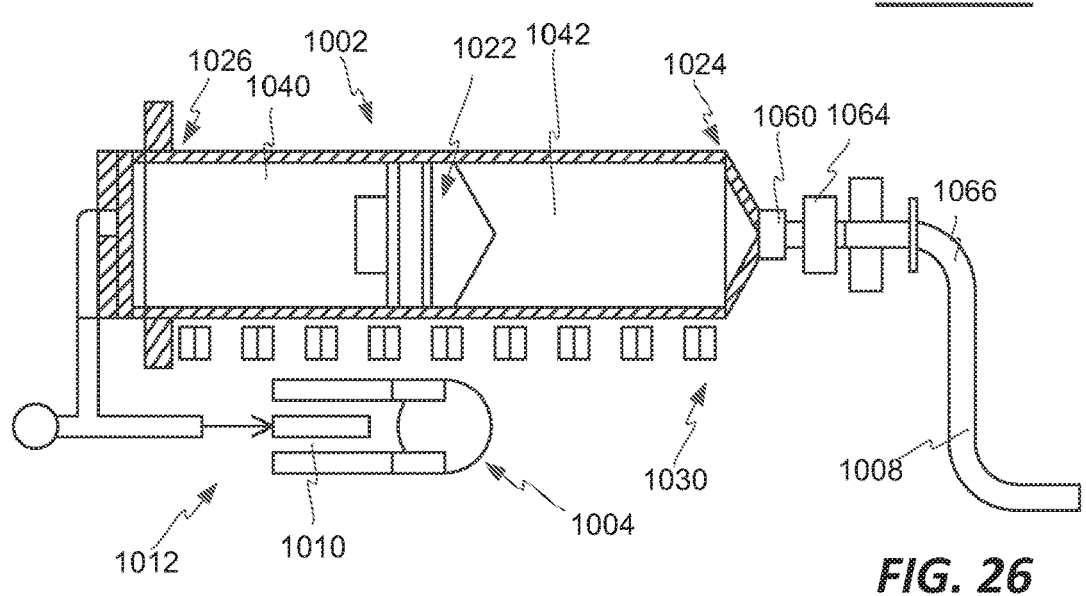

The method then continues with the controller 1014 operating the pump 1004 to pull a vacuum (see FIG. 23), which causes the plunger head assembly 1022 to move from the position (home positon) illustrated in FIG. 22 where the plunger head assembly 1022 is near the first end 1024 to a position as is illustrated in FIG. 24, wherein the plunger head assembly 1022 is nearer the second end 1026. Initially, the movement of the plunger head assembly 1022 causes air to enter the space 1042. The controller 1014 may use the fluid sensor 1016 to determine when the fluid enters the tip 1060 of the syringe and the position detector 1030 to determine the volume of air that will later need to be purged from the syringe 1002. This volume may be referred to as the tare volume.

The method continues with the controller 1014 operating the pump 1004 to move the plunger head assembly 1022 to draw a volume into the space 1042 that may be equal to the desired volume of fluid from the container 150 that is to be filled into the syringe 1002 (which may be referred to as the fill volume) and the volume of air initially drawn into the syringe 1002 at the beginning of the method (i.e., the tare volume). The volume that is the sum of the fill volume and the tare volume may be referred to as the stop volume. See FIG. 24.

At this point, it is desirable to remove the air that remains in the syringe 1002. The syringe 1002 may be oriented such that the tip 1060 is vertical to allow the air to move in the direction of the tip 1060. The controller 1014 then operates the pump 1004 to move the plunger head assembly 1022 in the direction of the first end 1024, thereby purging the air out of the space 1042 into the line 1066 in the direction of the container 150. See FIG. 25. The controller 1014 determines when the fluid in the space 1042 reaches the tip 1060, and then ceases operation of the pump 1004 and vents the space 1040 via the valve assembly 1012 and the vent 1010. See FIG. 26.

At this point, the syringe 1002 is filled. The tubing 1066 is heat sealed at the proximal end of the tubing 1066, and the remainder of the tubing 1066 is removed. The female leer-lock 1064 remains connected to the tip 1060 to cap the tip 1060. The filter assembly 1052 is removed from the syringe 1002 by unscrewing the filter assembly 1052 from the threaded aperture 1050 at the second end 1026 of the syringe 1002. A closed cap 1080 is screwed into the threaded aperture 1050 to complete the final assembly. See FIG. 27. The luer-lock 1064 and the cap 1080 are intended to remain in place during shipment and/or storage to preserve the sterile condition of the fluid. The syringe 1002 may then be subjected to additional processes, such as freezing.

At the time of use, the syringe 1002 is prepared for use, for example by thawing the syringe 1002 (where necessary) and by removing the closed cap 1080. The disc 1038 that is part of the plunger head assembly 1022 has a threaded connection hub 1082. A threaded first end 1084 of a plunger handle 1086 is screwed into the threaded connection hub 1082, and the syringe 1002 is ready for administration once the female luer-lock/cap 1064 is removed. See FIG. 28.

Thus, an improved method and system have been disclosed for the processing of biological cells and the filling of containers. The description provided above is intended for illustrative purposes only and is not intended to limit the scope of the invention to any specific method, system, or apparatus, or device described herein except as may be explicitly delineated above.

Other Aspects

Aspect 1. A filling system comprising a transfer set connectable to a source container; a plurality of filling stations each comprising at least one container connected to the transfer set and in selective fluid communication with the source container via the transfer set; a pump configured to transfer a product from the source container to the at least one container via the transfer set; and a controller coupled to the at least one filling station and the pump, the controller configured to operate each of the filling stations and the pump in concert to move fluid from the source container to the at least one container associated with at least one of the plurality of filling stations.

Aspect 2. The filling system according to Aspect 1, wherein each filling station comprises a valve that limits or permits fluid communication between the at least one container and the source container, and further comprising a pressure sensor coupled to the transfer set between the source container and the plurality of filling stations, the controller coupled to the pressure sensor, and configured to open the valve associated with only one of the plurality of filling stations, to operate the pump until the pressure sensor detects a spike in pressure in the transfer set, and to close the valve associated with the one of the plurality of filling stations after the pressure sensor detects a spike in the pressure in the transfer set.

Aspect 3. The filling system according to Aspect 1 or 2, wherein the at least one container at each of the plurality of filling stations is a rigid or semi-rigid container.

Aspect 4. The filling system according to Aspect 1, wherein each filling station comprises a valve that limits or permits fluid communication between the at least one container and the source container, and the pump is a syringe pump, the controller configured to open the valve associated with only one of the plurality of filling stations, to operate the syringe pump to transfer a specific volume of fluid from the source container to the at least one container of the one of the plurality of filling stations, and to close the valve associated with the one of the plurality of filling stations after the specific volume is pumped.

Aspect 5. The filling system according to Aspect 1, wherein each filling station comprises a valve that limits or permits fluid communication between the at least one container and the source container, and the pump is a syringe pump, the controller configured to open the valve associated with a first of the plurality of filling stations, to operate the syringe pump to transfer fluid from the source container to the at least one container of the one of the plurality of filling stations, to open the valve associated with a second of the plurality of filling stations, and after opening the valve associated with the second of the plurality of filling stations, to close the valve associated with the first of the plurality of filling stations.

Aspect 6. The filling system according to Aspect 5, wherein the controller is configured to close the valve associated with the first of the filling stations after at least one time interval elapses after the opening of the valve associated with the second of the plurality of filling stations.

Aspect 7. The filling system according to Aspect 1, further comprising a single valve assembly between the source container and the at least one container at each of the filling stations, the valve assembly coupled to the controller, the controller configured to operate the valve assembly such that the at least one container at only a first of the plurality of filling stations is in fluid communication with the source container, to operate the pump to transfer fluid from the source container to the at least one container of the first of the plurality of filling stations, to operate the valve assembly such that the at least one container at the first of the plurality of filling stations is not in fluid communication with the source container and the at least one container with a second of the plurality of filling stations is in fluid communication.

Aspect 8. The filling system according to Aspect 1, wherein the transfer set includes a plurality of lines, each one of the lines associated with the at least one container at one of the plurality of filling stations, and the valve assembly comprises a table on which the plurality of lines are arranged and a continuous surface that is disposed against all but one of the lines on the table to prevent fluid flow along those lines, fluid flow being permitted along the one of the lines.

Aspect 9. The filling system according to Aspect 8, wherein the table is planar, and the continuous surface is defined by a continuous band disposed between two spaced wheels.

Aspect 10. The filling system according to Aspect 8, wherein the table is a disc, and the continuous surface is defined by a continuous clamp disposed about the disc.

Aspect 11. The filling system according to Aspect 8, wherein the table is a disc, and the continuous surface is defined by a continuous band disposed about the disc.

Aspect 12. The filling system according to Aspect 1, further comprising a track and an indexer, each filling station disposed on the track and indexed along the track by the indexer between a first position out of alignment and not in fluid communication with the source container and a second position in alignment and in fluid communication with the source container.

Aspect 13. The filling system according to Aspect 12, wherein the indexer comprises a spring to move the filling station between the first position and the second position, and an actuator to selectively hold the filling station in the second position.

Aspect 14. A filling system for filling a pre-filled syringe from a source container, the filling system comprising a transfer set connectable to a source container; a syringe having a first end to a first side of a plunger head assembly detachably connected to the transfer set, and a second end to a second side of the plunger head assembly; a pump detachably connected to the second side of the plunger head assembly; and a controller coupled to the pump, the controller configured to operate the pump to move the plunger head assembly between the first end and the second end to fill the syringe.

Aspect 15. The filling system according to Aspect 14, wherein the controller is configured to operate the pump to move the plunger head assembly to the first end of the syringe, to operate the pump to move the plunger head assembly a first distance from the first end, and to operate the pump then to move the plunger head assembly a second distance toward the first end of the syringe.

Aspect 16. The filling system according to Aspect 15, further comprising a position detector and a fluid sensor disposed at the first end of the syringe, the position detector and the fluid sensor coupled to the controller, and wherein the controller is configured to determine when fluid first enters the syringe via the fluid sensor, to determine a position of the plunger head assembly via the position detector when the fluid first enters the syringe, and to determine the second distance in accordance with the position of the plunger head assembly when the fluid first enters the syringe.

Aspect 17. The filling system according to Aspect 16, wherein the position detector comprises a plurality of transmitter/sensor pairs and a reflector attached to the plunger head assembly.

Aspect 18. The filling system according to Aspect 16 or 17, further comprising a valve assembly disposed between the second end of the syringe and the pump, the pump comprising a vacuum output and a pressure output, and the controller coupled to the valve assembly to selectively couple the vacuum output or the pressure output to the second end of the syringe.

Aspect 19. The filling system according to Aspect 18, further comprising a vent, the valve assembly coupled to the vent, and the controller selectively coupling the second end of the syringe to the vent after operating the pump to move the plunger head assembly the second distance toward the first end of the syringe Aspect 20, The filling system according to any one of Aspects 14 to 19, wherein the second side of the plunger head assembly has a threaded connection to accept a threaded end of a plunger handle.

The invention claimed is:

1. A filling system for filling a pre-filled syringe from a source container, the filling system comprising:
a transfer set connectable to a source container;
a syringe including a syringe barrel and a plunger head assembly disposed in the syringe barrel, the syringe having a first end, the first end detachably connected to the transfer set, and a second end;
a pump detachably connected to only the second end;
a controller coupled to the pump, the controller configured to operate the pump to move the plunger head assembly to the first end of the syringe, to operate the pump to move the plunger head assembly a first distance from the first end, and to operate the pump to move the plunger head assembly a second distance toward the first end of the syringe after moving the plunger head assembly the first distance from the first end.

2. A filling system for filling a pre-filled syringe from a source container, the filling system comprising:
a transfer set connectable to a source container;
a syringe including a syringe barrel and a plunger head assembly disposed in the syringe barrel, the syringe having a first end, the first end detachably connected to the transfer set, and a second end;
a pump detachably connected to the second end;
a controller coupled to the pump, the controller configured to operate the pump to move the plunger head assembly to the first end of the syringe, to operate the pump to move the plunger head assembly a first distance from the first end, and to operate the pump then to move the plunger head assembly a second distance toward the first end of the syringe; and
a position detector and a fluid sensor disposed at the first end of the syringe, the position detector and the fluid sensor coupled to the controller,
wherein the controller is configured to determine when fluid first enters the syringe via the fluid sensor, to determine a position of the plunger head assembly via the position detector when the fluid first enters the syringe, and to determine the second distance in accordance with the position of the plunger head assembly when the fluid first enters the syringe.

3. The filling system according to claim 2, wherein the position detector comprises a plurality of transmitter/sensor pairs and a reflector attached to the plunger head assembly.

4. The filling system according to claim 2, further comprising a valve assembly disposed between the second end of the syringe and the pump, the pump comprising a vacuum output and a pressure output, and the controller coupled to the valve assembly to selectively couple the vacuum output or the pressure output to the second end of the syringe.

5. The filling system according to claim 4, further comprising a vent, the valve assembly coupled to the vent, and the controller selectively coupling the second end of the syringe to the vent after operating the pump to move the plunger head assembly the second distance toward the first end of the syringe.

6. The filling system according to claim 2, wherein a side of the plunger head assembly has a threaded connection to accept a threaded end of a plunger handle.

7. The filling system according to claim 1, further comprising:
a position detector disposed along the syringe barrel and a fluid sensor disposed at the first end of the syringe, the position detector and the fluid sensor coupled to the controller, and
wherein the controller is configured to determine when fluid first enters the syringe via the fluid sensor and to determine a position of the plunger head assembly via the position detector.

8. The filling system according to claim 7, wherein the position detector comprises a plurality of transmitter/sensor pairs and a reflector attached to the plunger head assembly.

9. The filling system according to claim 7, further comprising a valve assembly disposed between the second end of the syringe and the pump, the pump comprising a vacuum output and a pressure output, and the controller coupled to the valve assembly to selectively couple the vacuum output or the pressure output to the second end of the syringe.

10. The filling system according to claim 9, further comprising a vent, the valve assembly coupled to the vent, and the controller selectively coupling the second end of the syringe to the vent after operating the pump to move the plunger head assembly the second distance toward the first end of the syringe.

11. The filling system according to claim 1, wherein a side of the plunger head assembly has a threaded connection to accept a threaded end of a plunger handle.

* * * * *